(12) United States Patent
Thayumanavan et al.

(10) Patent No.: US 12,344,693 B2
(45) Date of Patent: Jul. 1, 2025

(54) LIPID-POLYMER BASED COMPLEXATION AND DELIVERY OF NUCLEIC ACIDS

(71) Applicant: University of Massachusetts, Boston, MA (US)

(72) Inventors: Sankaran Thayumanavan, Amherst, MA (US); Kingshuk Dutta, Amherst, MA (US)

(73) Assignee: University of Massachusetts, Westborough, MA (US)

( * ) Notice: Subject to any disclaimer, the term of this patent is extended or adjusted under 35 U.S.C. 154(b) by 308 days.

(21) Appl. No.: 17/892,637

(22) Filed: Aug. 22, 2022

(65) Prior Publication Data

US 2023/0081736 A1     Mar. 16, 2023

Related U.S. Application Data

(62) Division of application No. 16/849,943, filed on Apr. 15, 2020, now Pat. No. 11,434,317.

(60) Provisional application No. 62/849,353, filed on May 17, 2019, provisional application No. 62/834,939, filed on Apr. 16, 2019.

(51) Int. Cl.
| | | |
|---|---|---|
| C08F 299/04 | (2006.01) | |
| A61K 47/54 | (2017.01) | |
| A61K 47/58 | (2017.01) | |
| C08F 220/38 | (2006.01) | |
| B82Y 5/00 | (2011.01) | |

(52) U.S. Cl.
CPC .......... *C08F 299/04* (2013.01); *A61K 47/543* (2017.08); *A61K 47/58* (2017.08); *C08F 220/385* (2020.02); *B82Y 5/00* (2013.01)

(58) Field of Classification Search
CPC .. C08F 299/04; C08F 2438/03; A61K 47/543; B82Y 5/00
See application file for complete search history.

(56) References Cited

U.S. PATENT DOCUMENTS

| | | | |
|---|---|---|---|
| 9,592,302 B2* | 3/2017 | Thayumanavan | .. C08F 220/385 |
| 9,999,599 B2* | 6/2018 | Thayumanavan | ....... A61K 9/51 |
| 10,131,745 B2* | 11/2018 | Thayumanavan | ..... C08G 69/26 |
| 11,434,317 B2* | 9/2022 | Thayumanavan | ... A61K 47/543 |

* cited by examiner

*Primary Examiner* — Carlos A Azpuru
(74) *Attorney, Agent, or Firm* — Milstein Zhang & Wu LLC

(57) ABSTRACT

The invention provides novel polymers, crosslinked polymer-nucleic acid complexes, lipid-polymer-nucleic acid-based complexation and nanoassemblies, and nanoassembly-based intracellular delivery of nucleic acids and controlled release thereof upon degradation of the nanoassemblies in response to specific microenvironment in the cell, and compositions and methods of preparation and use thereof.

17 Claims, 20 Drawing Sheets

LIPID-POLYMER BASED COMPLEXATION AND DELIVERY OF NUCLEIC ACIDS

PRIORITY CLAIMS AND RELATED APPLICATION

This application is a divisional of and claims the benefit of priority to U.S. Ser. No. 16/849,943, filed Apr. 15, 2020, which claims the benefit of priority to U.S. Provisional Application Nos. 62/834,939, filed Apr. 16, 2019, and 62/849,353, filed May 17, 2019, the entire content of each of which is incorporated herein by reference for all purposes.

STATEMENT REGARDING FEDERALLY FUNDED RESEARCH OR DEVELOPMENT

This invention was made with government support under Grant No. W911NF-15-1-0568 and W911NF-13-1-0187 awarded by the U.S. Army Research Office. The Government has certain rights in the invention.

TECHNICAL FIELDS OF THE INVENTION

The invention generally relates to polymers, nanoparticles and nucleic acid delivery. More particularly, the invention relates to polymers, lipid-polymer-based complexation and nanoassemblies of nucleic acids, and controllably intracellular delivery and release upon degradation of the nanoassemblies in response to specific microenvironment, and compositions and methods of preparation and use thereof.

BACKGROUND OF THE INVENTION

Self-assembly that relies on non-covalent intermolecular interactions, comprising single or multi-component molecular building blocks, plays a fundamentally important role in many biological processes and in the development of novel functional materials. (Whitesides, et al 1991 *Science* 254 (5036), 1312-9; Zhang 2003 *Nat. Biotechnol.* 21 (10), 1171-1178.) However, designing and assembling multiple molecular entities to generate a predictable and controlled supramolecular assembly have considerable challenges; but if achieved, this can propel the design of materials with functional capabilities that are currently not attainable.

Although discovery of small interfering RNA (siRNA), a potential gene silencing agent, has created attractive opportunities targeting a wide array of diseases, RNAi technology has produced only one drug approved for clinical use. (Zimmermann, et al. 2006 *Nature* 441 (7089), 111-114; Li, et al. 2018 *Proc. Natl. Acad. Sci. U.S.A.* 115 (12), E2696-E2705; Biswas, et al. 2019 *ACS Appl. Mater. Interfaces* 11 (5), 4719-4736; *Nature biotechnology* 2018, 36, 775.)

Poor cellular internalization, serum instability, rapid clearance, severe cytotoxicity and potential immunological flare-ups have been identified as the critical barriers for such promising technology. Potential solutions like, chemically modified siRNAs and viral vectors have yet to overcome issues owing to cytotoxicity, stability, immunogenicity and reduced silencing ability upon structural modifications. (Nguyen, et al. 2012 *Acc. Chem. Res.* 45 (7), 1153-1162; Wang, et al. 2010 *Aaps J.* 12 (4), 492-503; Gallas, et al. 2013 *Chem. Soc. Rev.* 42 (20), 7983-7997; Majumder, et al. 2018 *Chem. Commun.* 54 (12), 1489-1492; Roy, et al. 2009 *Biomacromolecules* 10 (8), 2189-93; Zheng, et al. 2012 *ACS Nano* 6 (11), 9447-54; Xue, et al. 2014 *Nanomedicine (London, U. K.)* 9 (2), 295-312; Wang, et al. 2016 *Chem. Commun.* 52 (6), 1194-1197.)

Interestingly, non-viral approaches, based on electrostatic complexation of nucleic acids using cationic lipids, peptides, nanoparticles, or polymers, have the potential to resolve the major reported issues. However, the key obstacle in these carrier-based delivery systems is the adverse side effects originated from the cationic charge mediated alteration in membrane potentials of cellular organelles and non-specific interactions with negatively charged serum proteins. (Xue, et al. 2014 *Nanomedicine (London, U. K.)* 9 (2), 295-312; Wagner 2012 *Acc. Chem. Res.* 45 (7), 1005-1013; Tai, et al. 2017 *Adv. Drug Delivery Rev.* 110-111, 157-168; Dunn, et al. 2012 *J. Am. Chem. Soc.* 134 (17), 7423-30; Freyer, et al. 2017 *J Polym Sci Pol Chem* 55 (19), 3167-3174; Ripoll, et al. 2016 *ACS Appl. Mater. Interfaces* 8 (45), 30665-30670; Shen, et al. 2012 *Chem Mater* 24 (1), 230-235; Lv, et al. 2006 *J. Control Release* 114 (1), 100-9; Hunter 2006 *Adv. Drug Delivery Rev.* 58 (14), 1523-31.)

To address this, two interesting approaches, viz. charge-masking strategies and spherical nucleic acids have been reported wherein cationic charges are masked and negatively charged nucleic acids are decorated on surfaces, respectively. In addition to the non-cationic surface display, the degradable cationic blocks offer opportunities to mitigate toxicity issues associated with cationic polymers as well. (akae, et al. 2008 *J. Am. Chem. Soc.* 130 (18), 6001-6009; Sizovs, et al. 2013 *J. Am. Chem. Soc.* 135 (41), 15417-15424; Rosi, et al. 2006 *Science* 312 (5776), 1027-30; Cohen, et al. 2010 *Adv. Mater.* 22 (32), 3593-+; Samarajeewa, et al. 2013 *Biomacromolecules* 14 (4), 1018-27; McKinlay, et al. 2017 *Proc. Natl. Acad. Sci. U.S.A.* 114 (4), E448-E456; Geng, et al. 2018 *Chem. Mater.* 30 (22), 8164-8169.)

Mimicking viral mechanism of cellular entry, another polymeric delivery agent, virus-inspired polymer for endosomal release, is developed with a hydrophilic cationic block and an endosomolytic peptide displayed only under acidic pH. In a significant departure from the conventional approaches, direct decoration of a high density of nucleic acids themselves as surface functionalities on nanoparticles and polymers have produced negatively charged nanostructures with good cellular internalization and gene silencing capabilities. Despite these advances, there still exists a need for RNAi-based therapeutic approaches that would retain the key advantages of non-viral carriers, while mitigating their shortcomings. (Rosi, et al. 2006 *Science* 312 (5776), 1027-30; Cheng, et al. 2016 *Angew. Chem., Int. Ed* 55 (39), 12013-12017; Lu, et al. 2016 *J. Am. Chem. Soc.* 138 (29), 9097-100.)

Accordingly, an ongoing need remains for an effective delivery vehicle for nucleic acids, one that is highly robust and effective and at the same time with low toxicity and long intracellular half-life enabling practical therapeutic applications.

SUMMARY OF THE INVENTION

The invention provides polymers and polymeric nanogels in which nucleic acid molecules can be stably entrapped or encapsulated and are controllably delivered and released upon degradation of the nanoassembly in response to specific microenvironment triggers, and compositions and methods of preparation and use thereof.

For example, a unique siRNA encapsulation and intracellular delivery approach is disclosed herein that employs a new symbiotic self-assembly strategy of a polymer, siRNA and lipid molecules. In this approach, the initial complexation with the siRNA is made possible through classical electrostatic interactions. A key feature is that this interaction was carried out in a relatively apolar media that not only enhances the binding affinity between the polymer and the siRNA, but also facilitates the retention of siRNA within the in situ generated polymer 'cage'. Note that the electrostatic complex is converted to a physically-incarcerating capsule through a crosslinking reaction, which concurrently removes the positive charge in the polymer. As the positive charges are being removed, but before the crosslinking reinforcement is fully in place, the siRNA molecules could escape the complex. However, the siRNA remains stably encapsulated, because the bulk environment of this in situ crosslinking reaction is apolar and incompatible. This structure is then finally camouflaged by the coating of a zwitterionic lipid that also imparts biocompatibility and endosomolytic ability. Efficient gene-silencing mediated by the designed nanoassembly provides evidence for successful integration and leverage of the built-in molecular features.

In one aspect, the invention generally relates to a copolymer comprising structural units of:

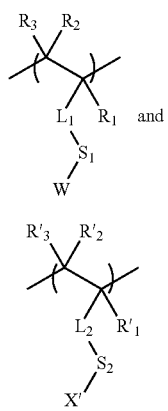

(I)

(II)

wherein
each of $R_1$ and $R'_1$ is independently a hydrogen, $C_1$-$C_{12}$ alkyl group, or halogen;
each of $R_2$, $R'_2$, $R_3$, and $R'_3$ is independently a hydrogen, $C_1$-$C_{16}$ alkyl, $C_1$-$C_{16}$ alkyloxy, or halogen;
each of $L_1$ and $L_2$ is independently a linking group;
each of $S_1$ and $S_2$ is independently a single bond or a spacer group;
W is a hydrophobic group; and
X' is a group comprising a crosslinking moiety and a cationic group.

In another aspect, the invention generally relates to a polymer-nucleic acid complex, comprising: a block or random copolymer comprising structural units of:

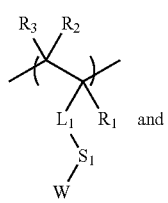

(I)

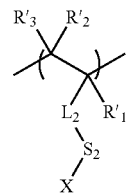

(IV)

wherein
each of $R_1$ and $R'_1$ is independently a hydrogen, $C_1$-$C_{12}$ alkyl group, or halogen;
each of $R_2$, $R'_2$, $R_3$, and $R'_3$ is independently a hydrogen, $C_1$-$C_{16}$ alkyl, $C_1$-$C_{16}$ alkyloxy, or halogen;
each of $L_1$ and $L_2$ is independently a linking group;
each of $S_1$ and $S_2$ is independently a single bond or a spacer group;
W is a hydrophobic group;
X is a group comprising a crosslinking moiety, and
a nucleic acid molecule complexed to the block or random copolymer.

In yet another aspect, the invention generally relates to a crosslinked polymer-nucleic acid complex, comprising: a crosslinked block or random copolymer comprising structural units of:

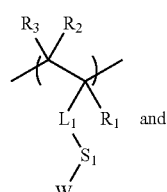

(I)

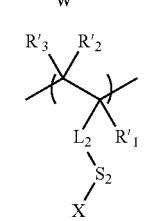

(IV)

wherein
each of $R_1$ and $R'_1$ is independently a hydrogen, $C_1$-$C_{12}$ alkyl group, or halogen;
each of $R_2$, $R'_2$, $R_3$, and $R'_3$ is independently a hydrogen, $C_1$-$C_{16}$ alkyl, $C_1$-$C_{16}$ alkyloxy, or halogen;
each of $L_1$ and $L_2$ is independently a linking group;
each of $S_1$ and $S_2$ is independently a single bond or a spacer group;
W is a hydrophobic group;
X is a group comprising a crosslinking moiety, and a nucleic acid molecule entrapped in the crosslinked block or random copolymer.

In yet another aspect, the invention generally relates to a molecular assembly, comprising: a crosslinked polymer-nucleic acid complex comprising a nucleic acid encapsulated in a crosslinked polymer network; and a coating on the crosslinked polymer-nucleic acid complex, wherein the coating comprises a zwitterionic lipid and a PEGylated lipid.

In yet another aspect, the invention generally relates to a method for forming a molecular assembly, comprising: mixing an amphiphilic polymer and a nucleic acid to form a polymer-nucleic acid complex; crosslinking the polymer in the polymer-nucleic acid complex to form a crosslinked polymer network entrapping the nucleic acid therein; and contacting the crosslinked polymer-nucleic acid complex with a zwitterionic lipid and a PEGylated lipid to form a coating on the crosslinked polymer-nucleic acid complex, wherein the coating comprises the zwitterionic lipid and the PEGylated lipid.

In yet another aspect, the invention generally relates to a method for delivering a nucleic acid molecule, comprising: forming a molecular assembly disclosed herein; and directing the molecular assembly to a target site.

DEFINITIONS

Figure 1:
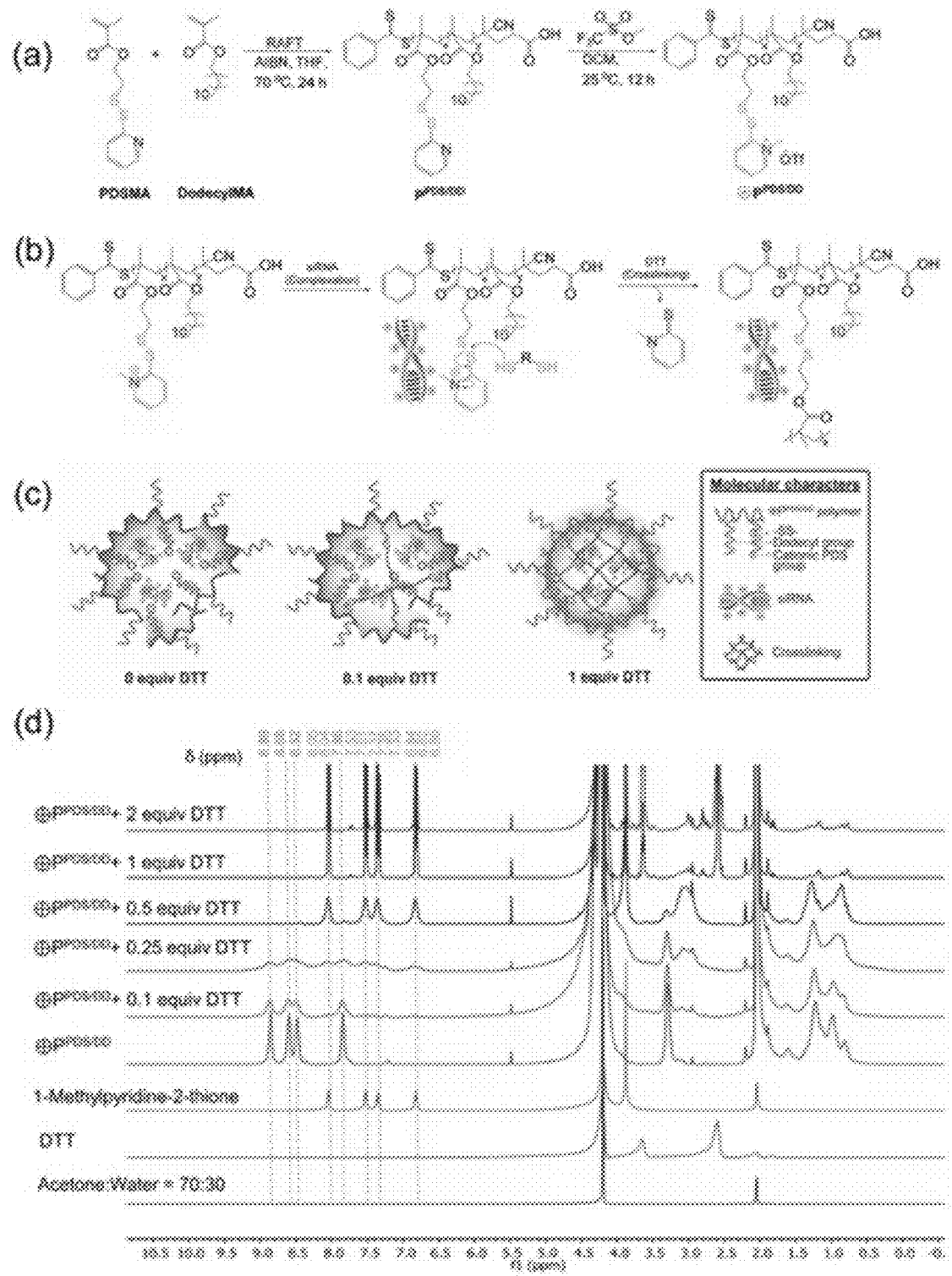
FIG. 1. (a) Synthesis of p(PDSMA-co-DodecylMA) polymer (PPDS/DD) and post-polymerization modification to install cationic charge yielding ⊕PPDS/DD polymer; (b) Reaction scheme for preparation of non-cationic L-siP nanoparticles via disulfide based crosslinking; (c) Schematic representation of differentially crosslinked polymer-siRNA assemblies; (d) 1H NMR spectra of ⊕PPDS/DD polymer treated with different amounts of DTT for crosslinking in acetone:water (deuterated)=70:30; (e) Symbiotic self-assembly strategy to construct L-siP nanoassembly and its key molecular components (Scheme 1).
Figure 1:
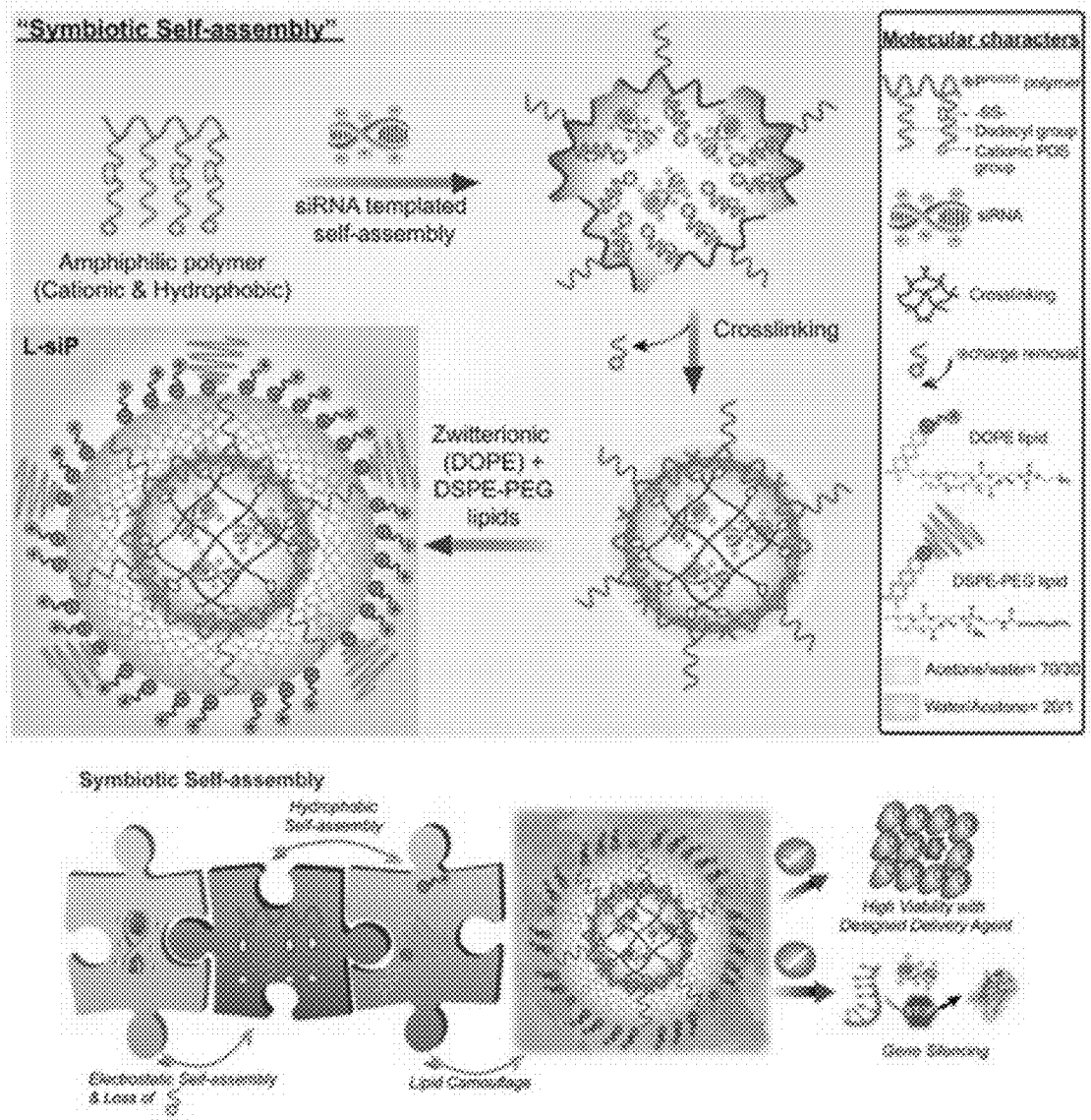

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Definitions of specific functional groups and chemical terms are described in more detail below. When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

Where substituent groups are specified by their conventional chemical formulae, written from left to right, they equally encompass the chemically identical substituents that would result from writing the structure from right to left, e.g., —C(=O)—O— is equivalent to —O—C(=O)—.

Structures of compounds of the invention are limited by principles of chemical bonding known to those skilled in the art. Accordingly, where a group may be substituted by one or more of a number of substituents, such substitutions are selected so as to comply with principles of chemical bonding and to give compounds that are not inherently unstable and/or would be known to one of ordinary skill in the art as likely to be unstable under ambient conditions (e.g., aqueous, neutral, and several known physiological conditions).

As used herein, the term "alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a $C_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents.

As used herein, the term "alkoxy" refers to the group —O-alkyl, including from 1 to 10 carbon atoms ($C_{1-10}$) of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. Lower alkoxy refers to alkoxy groups containing one to six carbons. In some embodiments, $C_{1-3}$ alkoxy is an alkoxy group that encompasses both straight and branched chain alkyls of from 1 to 3 carbon atoms. Unless stated otherwise in the specification, an alkoxy group can be optionally substituted by one or more substituents.

As used herein, the terms "aromatic" or "aryl" refer to a radical with 6 to 14 ring atoms (e.g., $C_{6-14}$ aromatic or $C_{6-14}$ aryl) that has at least one ring having a conjugated pi electron system which is carbocyclic (e.g., phenyl, fluorenyl, and naphthyl). In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl moiety can be optionally substituted by one or more substituents.

As used herein, the term "halogen" refers to fluorine (F), chlorine (Cl), bromine (Br), or iodine (I). As used herein, the term "halide" or "halo", means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

As used herein, the term "nucleic acid" refers to polymeric forms of nucleotides, including ribonucleotides as well as deoxyribonucleotides, of any length. They can include both double-, single-stranded or triple helical sequences and include, but are not limited to, cDNA from viral, prokaryotic, and eukaryotic sources; mRNA; genomic DNA sequences from viral (e.g., DNA viruses and retroviruses) or prokaryotic sources; RNAi; cRNA; antisense molecules; recombinant polynucleotides; ribozymes; and synthetic DNA sequences. The term also captures sequences that include any of the known base analogs of DNA and RNA. Nucleotides can be referred to by their commonly accepted single-letter codes. Exempary nucleic acid molecules include double-stranded RNA (dsRNA), small interfering RNA (siRNA), messenger RNA (mRNA), non-coding RNA (ncRNA), microRNA, catalytic RNA, guide RNA (gRNA), DNAs, oligonucleotides, aptamers, genes, plasmids, and derivatives or analogs thereof.

As used herein, the terms "isolated" or "purified" refer to a material that is substantially or essentially free from components that normally accompany it in its native state. Purity and homogeneity are typically determined using analytical chemistry techniques such as polyacrylamide gel electrophoresis or high-performance liquid chromatography.

DETAILED DESCRIPTION OF THE INVENTION

The present invention provides an effective delivery vehicle for nucleic acids. The nucleic acid delivery system disclosed herein is highly robust and effective and at the same time with low toxicity and long intracellular half-life enabling practical therapeutic applications. In addition, the copolymers, nanogels and delivery molecular assmeblies of the invention can be prepared via simple and reliable synthetic techniques.

More particularly, disclosed herein is a new three-component self-assembling system, where the parts are interdependent in the formation of the nanoassembly. In addition to demonstrating the formation and the characterization of such an assembly, the utility of such a nanostructure in addressing current toxicity and cellular delivery challenges involving small interfering RNA (siRNA) molecules has been investigated.

A unique aspect of the invention is that it employs a noncationic approach wherein the cationic charge is irreversibly removed after encapsulation of siRNA without compromising stability and activity of the nucleic acid. To this end, a unique and well-defined 'symbiotic self-assembly' approach was designed to efficiently self-assemble a polymer, lipids, and the nucleic acid to form stable lipid decorated siRNA-polymer (L-siP) nanoassemblies (Scheme 1).

The invention employs a novel 'symbiotic self-assembly' strategy that integrates the advantages of biocompatible lipids with a structurally robust polymer to efficiently encapsulate and deliver siRNAs. None of the assembling components are capable of self-assembly, but can form well-defined nanostructures in the presence of others.

The disclosed system enjoys many distinct advantages: (i) the high binding affinity results in efficient capture of siRNAs inside the assemblies; (ii) although electrostatics is utilized to capture the siRNAs, the residual assembly is non-cationic due to an in situ crosslinking protocol that removes the cationic charge on the polymer, yet incarcerates the siRNA; (iii) the surface charge of the assemblies is non-cationic; and (iv) the siRNA can be released using a trigger that corresponds to the operational environment of the cargo.

The conditions of the self-assembly process are simple, but have been chosen such that it offers the ability to arrive at a system that is non-cationic for mitigating carrier-based cytotoxicity, efficiently encapsulate siRNA to minimize cargo loss, effectively camouflaged to protect the siRNA from nuclease degradation, and efficiently escape the endosome to cause gene knockdown. The L-siP nanoassembly formation and its disassembly in the presence of an intracellular trigger have been extensively characterized experimentally and through computational modeling. The complexes have been evaluated for delivery of four different siRNA molecules in three different cell lines, where an efficient gene knock-down is demonstrated. The reported generalized strategy has the potential to make an impact in the development of a safe and effective delivery agent for RNAi mediated gene therapy that holds the promise of targeting several hard-to-cure diseases. Moreover, the same strategy can be used for delivering other nucleic acids such mRNA, miRNA, DNA, and nucleic acid aptamers.

In one aspect, the invention generally relates to a copolymer comprising structural units of:

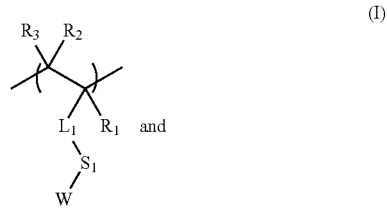 and

-continued

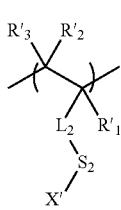
(II)

wherein
each of $R_1$ and $R'_1$ is independently a hydrogen, $C_1$-$C_{12}$ alkyl group, or halogen;
each of $R_2$, $R'_2$, $R_3$, and $R'_3$ is independently a hydrogen, $C_1$-$C_{16}$ alkyl, $C_1$-$C_{16}$ alkyloxy, or halogen;
each of $L_1$ and $L_2$ is independently a linking group;
each of $S_1$ and $S_2$ is independently a single bond or a spacer group;
W is a hydrophobic group; and
X' is a group comprising a crosslinking moiety and a cationic group.

In certain embodiments, the copolymer further comprises a structural unit of:

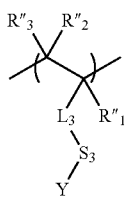
(III)

wherein
$R''_1$ is a hydrogen, $C_1$-$C_{12}$ alkyl group, or halogen;
each of $R''_2$ and $R''_3$ is independently a hydrogen, $C_1$-$C_{16}$ alkyl, $C_1$-$C_{16}$ alkyloxy, or halogen;
$L_3$ is a linking group;
$S_3$ is a single bond or a spacer group; and
Y is a non-crosslinking group.

In certain embodiments, the copolymer is a random copolymer.

In certain embodiments, the copolymer is a block copolymer.

In certain embodiments, the ratio of (I) to (II) in the copolymer, i:j, is in the range from about 5:95 to about 95:5. In certain embodiments, the ratio of i:j is in the range from about 10:90 to about 90:10. In certain embodiments, the ratio of i:j is in the range from about 20:80 to about 80:20.

In certain embodiments, the copolymer has a molecular weight ($M_n$) from about 1,000 to about 200,000 (e.g., from about 1,000 to about 150,000, from about 1,000 to about 100,000, from about 1,000 to about 50,000, from about 5,000 to about 200,000, from about 10,000 to about 200,000, from about 50,000 to about 200,000, from about 100,000 to about 200,000).

W is a group that comprises hydrophobic groups, such as hydrocarbons that include —$CH_2$— chains and rings. These substances lack the ability to hydrogen bond and their surface free energy is relatively low hence making them hydrophobic. In certain embodiments, W comprises a $C_1$-$C_{30}$ (e.g., $C_1$-$C_{30}$, $C_6$-$C_{30}$, $C_9$-$C_{30}$, $C_{12}$-$C_{30}$, $C_{15}$-$C_{30}$, $C_{18}$-$C_{30}$, $C_6$-$C_{24}$, $C_{12}$-$C_{24}$, $C_{15}$-$C_{24}$, $C_{10}$-$C_{20}$, $C_9$-$C_{15}$, $C_{12}$-$C_{15}$) linear, branched or cyclic alkyl group.

In certain embodiments, each of $L_1$, $L_2$ and $L_3$ is independently a

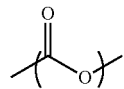

or an

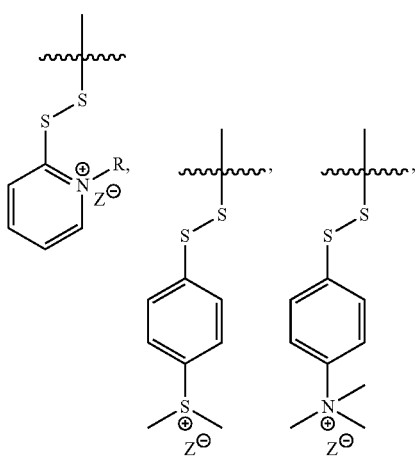

group.

X' is a group that comprises a crosslinking moiety and a cationic group. Crosslinking herein refers to forming of a bond that links one polymer chain to another polymer chain, either within the same polymer molecule or between different polymer molecules. A crosslinking moiety refers to a chemical moiety that is either capable of forming a crosslinking bond or is a chemical moiety that is crosslinked, either within the same polymer molecule or between different polymer molecules. A non-crosslinking group refers to a chemical group unable to form a crosslinking bond in the context of disclosed invention.

In certain embodiments, X' comprises a disulfide group. In certain embodiments, X' comprises a quaternary ammonium cation. In certain embodiments, X' comprises a sulfonium cation.

Any suitable counter ions may be employed, e.g., halide, acetate, carbonate, sulfate, mesylate, maleate, citrate, just to name a few).

In certain embodiments, X' comprises a group selected from:

-continued

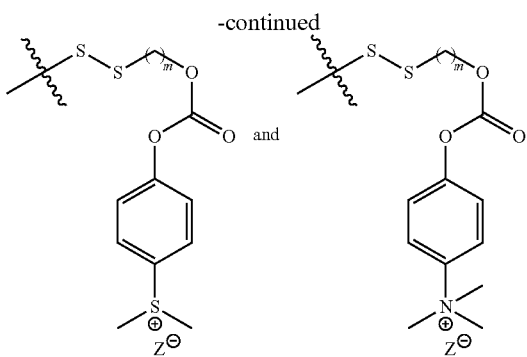

and wherein R is a $C_1$-$C_{15}$ (e.g., $C_1$-$C_{12}$, $C_1$-$C_6$, $C_1$-$C_3$, $C_1$) alkyl group, and $Z^-$ is a counter ion.

In another aspect, the invention generally relates to a polymer-nucleic acid complex, comprising: a block or random copolymer comprising structural units of:

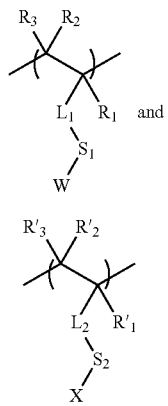

(I)

(IV)

wherein
each of $R_1$ and $R'_1$ is independently a hydrogen, $C_1$-$C_{12}$ alkyl group, or halogen;
each of $R_2$, $R'_2$, $R_3$, and $R'_3$ is independently a hydrogen, $C_1$-$C_{16}$ alkyl, $C_1$-$C_{16}$ alkyloxy, or halogen;
each of $L_1$ and $L_2$ is independently a linking group;
each of $S_1$ and $S_2$ is independently a single bond or a spacer group;
W is a hydrophobic group;
X is a group comprising a crosslinking moiety, and
a nucleic acid molecule complexed to the block or random copolymer.

In certain embodiments of the polymer-nucleic acid complex, the block or random copolymer further comprises the structural unit of:

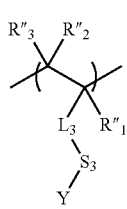

(III)

wherein
$R''_1$ is a hydrogen, $C_1$-$C_{12}$ alkyl group, or halogen;
each of $R''_2$ and $R''_3$ is independently a hydrogen, $C_1$-$C_{16}$ alkyl, $C_1$-$C_{16}$ alkyloxy, or halogen;
$L_3$ is a linking group;
$S_3$ is a single bond or a spacer group; and
Y is a non-crosslinking group.

In yet another aspect, the invention generally relates to a crosslinked polymer-nucleic acid complex, comprising: a crosslinked block or random copolymer comprising structural units of:

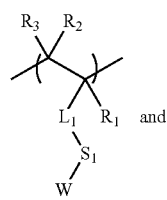

(I)

and

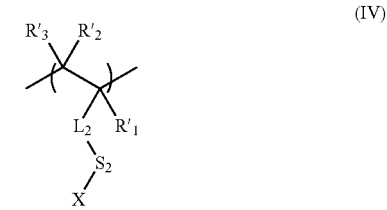

(IV)

wherein
each of $R_1$ and $R'_1$ is independently a hydrogen, $C_1$-$C_{12}$ alkyl group, or halogen;
each of $R_2$, $R'_2$, $R_3$, and $R'_3$ is independently a hydrogen, $C_1$-$C_{16}$ alkyl, $C_1$-$C_{16}$ alkyloxy, or halogen;
each of $L_1$ and $L_2$ is independently a linking group;
each of $S_1$ and $S_2$ is independently a single bond or a spacer group;
W is a hydrophobic group;
X is a group comprising a crosslinking moiety, and
a nucleic acid molecule entrapped in the crosslinked block or random copolymer.

The term "entrapped" as used herein refers to the encapsulation, immobilization or otherwise capture of a nucleic acid molecule by the crosslinked block or random copolymer.

In certain embodiments of the crosslinked polymer-nucleic acid complex, the block or random copolymer further comprises the structural unit of:

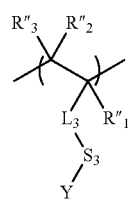

(III)

wherein
$R''_1$ is a hydrogen, $C_1$-$C_{12}$ alkyl group, or halogen;
each of $R''_2$ and $R''_3$ is independently a hydrogen, $C_1$-$C_{16}$ alkyl, $C_1$-$C_{16}$ alkyloxy, or halogen;
$L_3$ is a linking group;
$S_3$ is a single bond or a spacer group; and
Y is a non-crosslinking group.

In certain embodiments of the crosslinked polymer-nucleic acid complex, X comprises a crosslinked group.

In certain embodiments of the crosslinked polymer-nucleic acid complex, X comprises a group capable of forming a crosslinking bond.

In certain embodiments of the crosslinked polymer-nucleic acid complex, the nucleic acid molecule is selected from single-stranded or double-stranded RNA or DNA, and derivatives or analogs thereof. In certain embodiments, the nucleic acid molecule is selected from dsRNA, siRNA, mRNA, ncRNA, microRNA, catalytic RNA, gRNA, DNAs, oligonucleotides, aptamers, genes, plasmids, and derivatives or analogs thereof. In certain embodiments, the nucleic acid molecule is an siRNA.

In certain embodiments of the crosslinked polymer-nucleic acid complex, the copolymer is a random copolymer.

In certain embodiments of the crosslinked polymer-nucleic acid complex, the copolymer is a block copolymer.

In certain embodiments, the ratio of (I) to (IV) in the copolymer, i:j, is in the range from about 5:95 to about 95:5. In certain embodiments, the ratio of i:j is in the range from about 10:90 to about 90:10. In certain embodiments, the ratio of i:j is in the range from about 20:80 to about 80:20.

In certain embodiments, W comprises a $C_1$-$C_{30}$ (e.g., $C_1$-$C_{30}$, $C_6$-$C_{30}$, $C_9$-$C_{30}$, $C_{12}$-$C_{30}$, $C_{15}$-$C_{30}$, $C_{18}$-$C_{30}$, $C_6$-$C_{24}$, $C_{12}$-$C_{24}$, $C_{15}$-$C_{24}$, $C_{10}$-$C_{20}$, $C_9$-$C_{15}$, $C_{12}$-$C_{15}$) linear, branched or cyclic alkyl group.

In certain embodiments, each of $L_1$, $L_2$ and $L_3$ is independently a

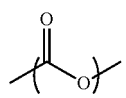

or an

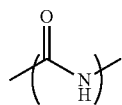

group.

In certain embodiments, X comprises a disulfide group.

In certain embodiments, the block or random copolymer further comprises the structural unit of:

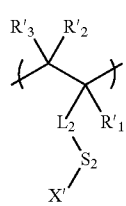

(II)

wherein X' comprises a group selected from:

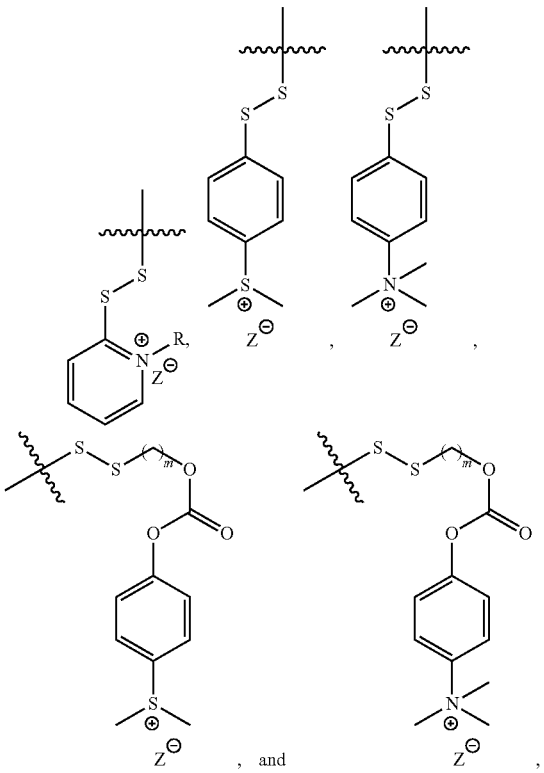

wherein R is a $C_1$-$C_{15}$ (e.g., $C_1$-$C_{12}$, $C_1$-$C_6$, $C_1$-$C_3$, $C_1$) alkyl group, and $Z^-$ is a counter ion.

In certain embodiments of the crosslinked polymer-nucleic acid complex, the polymer host comprises a network of a block or random copolymer having the structural formula:

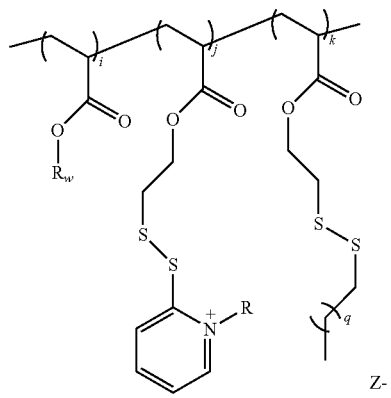

wherein $R_w$ is a $C_1$-$C_{30}$ (e.g., $C_1$-$C_{30}$, $C_6$-$C_{30}$, $C_9$-$C_{30}$, $C_{12}$-$C_{30}$, $C_{15}$-$C_{30}$, $C_{18}$-$C_{30}$, $C_6$-$C_{24}$, $C_{12}$-$C_{24}$, $C_{15}$-$C_{24}$, $C_{10}$-$C_{20}$, $C_9$-$C_{15}$, $C_{12}$-$C_{15}$) linear, branched or cyclic alkyl group, q is an integer from about 1 to about 10 (e.g., from about 1 to about 6, from about 1 to about 3) and R is a $C_1$-$C_{15}$ (e.g., $C_1$-$C_{12}$, $C_1$-$C_6$, $C_1$-$C_3$, $C_1$) alkyl group, and $Z^-$ is a counter ion. Any suitable counter ions may be employed, e.g., halide, acetate, carbonate, sulfate, mesylate, maleate, citrate, just to name a few).

In certain embodiments, the crosslinked polymer-nucleic acid complex is crosslinked both inter-molecularly and intra-molecularly.

In certain embodiments, the crosslinked polymer-nucleic acid complex is adapted to de-crosslink partially or completely upon contact with a biological or chemical stimulus.

In certain embodiments of the crosslinked polymer-nucleic acid complex, X comprises a pH-sensitive functional group.

In certain embodiments of the crosslinked polymer-nucleic acid complex, X comprises a redox-sensitive functional group.

In yet another aspect, the invention generally relates to a molecular assembly, comprising: a crosslinked polymer-nucleic acid complex comprising a nucleic acid encapsulated in a crosslinked polymer network; and a coating on the crosslinked polymer-nucleic acid complex, wherein the coating comprises a zwitterionic lipid and a PEGylated lipid.

The lipid coating (or membrane) comprises a zwitterionic lipid and a PEGylated lipid, i.e., a lipid covalently conjugated to or modified with a polyethylene glycol (PEG). PEGs are oligomers or polymers of ethylene glycol and are inert, nontoxic and biodegradable organic polymers. The terms "PEG", "PEG Unit" or "polyethylene glycol" are used herein to refer to an organic moiety comprised of repeating ethylene-oxy subunits.

The term "lipid" is used herein to refer to hydrophobic or amphiphilic molecules that are soluble in nonpolar solvents. The amphiphilic nature of certain lipids allows them to form structures such as vesicles, multilamellar/unilamellar liposomes, or membranes in an aqueous environment. Lipids may be, for example, fatty acids, glycerolipids, glycerophospholipids, sphingolipids, saccharolipids, and polyketides; and sterol lipids and prenol lipids.

As used herein, the term "zwitterionic lipid" refers to a lipid molecule that comprises functional groups, of which at least one has a positive and one has a negative electrical charge, with the total net charge of the entire lipid molecule being zero. In certain embodiments of the molecular assembly, the zwitterionic lipid comprises a zwitterionic group is selected from the group consisting of:

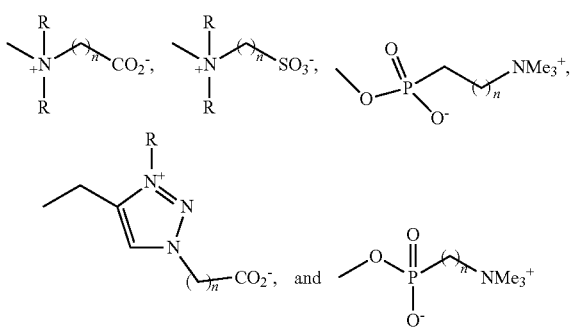

wherein each R is hydrogen or a $C_1$-$C_{15}$ (e.g., $C_1$-$C_{12}$, $C_1$-$C_9$, $C_1$-$C_6$, $C_1$-$C_3$, $C_3$-$C_{15}$, $C_6$-$C_{15}$, $C_9$-$C_{15}$, $C_3$-$C_9$, $C_6$-$C_{12}$) alkyl group; n is independently an integer from about 1 to about 12.

In certain embodiments of the molecular assembly, the crosslinked polymer-nucleic acid complex comprises: a crosslinked block or random copolymer comprising structural units of:

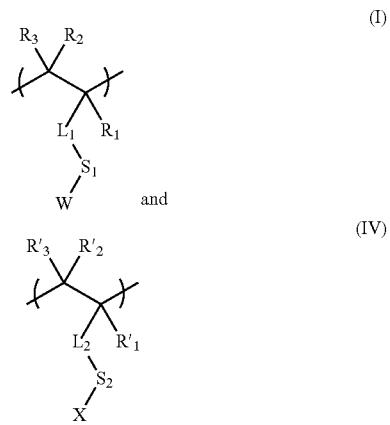

wherein
each of $R_1$ and $R'_1$ is independently a hydrogen, $C_1$-$C_{12}$ alkyl group, or halogen;
each of $R_2$, $R'_2$, $R_3$, and $R'_3$ is independently a hydrogen, $C_1$-$C_{16}$ alkyl, $C_1$-$C_{16}$ alkyloxy, or halogen;
each of $L_1$ and $L_2$ is independently a linking group;
each of $S_1$ and $S_2$ is independently a single bond or a spacer group;
W is a hydrophobic group;
X is a group comprising a crosslinking moiety, and a nucleic acid molecule entrapped in the crosslinked block or random copolymer.

In certain embodiments of the molecular assembly, the block or random copolymer further comprises the structural unit of:

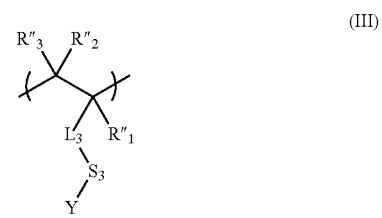

wherein
$R''_1$ is a hydrogen, $C_1$-$C_{12}$ alkyl group, or halogen;
each of $R''_2$ and $R''_3$ is independently a hydrogen, $C_1$-$C_{16}$ alkyl, $C_1$-$C_{16}$ alkyloxy, or halogen;
$L_3$ is a linking group;
$S_3$ is a single bond or a spacer group; and
Y is a non-crosslinking group.

In certain embodiments of the molecular assembly, X comprises a crosslinked group.

In certain embodiments of the molecular assembly, X comprises a group capable of forming a crosslinking bond.

In certain embodiments of the molecular assembly, the nucleic acid molecule is selected from single-stranded or double-stranded RNA or DNA, and derivatives or analogs thereof.

In certain embodiments of the molecular assembly, the nucleic acid molecule is selected from dsRNA, siRNA, mRNA, ncRNA, microRNA, catalytic RNA, gRNA, DNAs, oligonucleotides, aptamers, genes, plasmids, and derivatives or analogs thereof.

In certain embodiments of the molecular assembly, the nucleic acid molecule is an siRNA.

In certain embodiments of the molecular assembly, the copolymer is a random copolymer.

In certain embodiments of the molecular assembly, the copolymer is a block copolymer.

In certain embodiments of the molecular assembly, W comprises a $C_1$-$C_{30}$ (e.g., $C_1$-$C_{30}$, $C_6$-$C_{30}$, $C_9$-$C_{30}$, $C_{12}$-$C_{30}$, $C_{15}$-$C_{30}$, $C_{18}$-$C_{30}$, $C_6$-$C_{24}$, $C_{12}$-$C_{24}$, $C_{15}$-$C_{24}$, $C_{10}$-$C_{20}$, $C_9$-$C_{15}$, $C_{12}$-$C_{15}$) linear, branched or cyclic alkyl group.

In certain embodiments of the molecular assembly, each of $L_1$, $L_2$ and $L_3$ is independently a

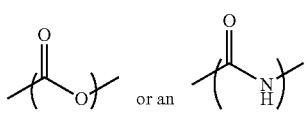

group.

In certain embodiments of the molecular assembly, X comprises a disulfide group.

In certain embodiments of the molecular assembly, the block or random copolymer further comprises the structural unit of:

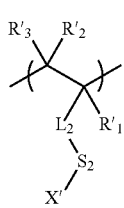

(II)

wherein X' comprises a group selected from:

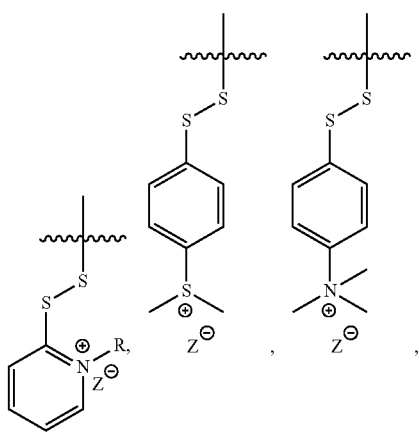

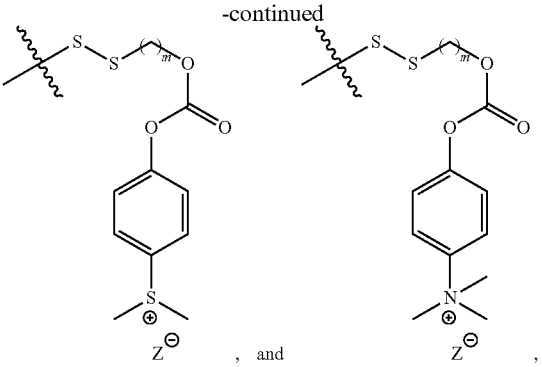

wherein R is a $C_1$-$C_{15}$ (e.g., $C_1$-$C_{12}$, $C_1$-$C_6$, $C_1$-$C_3$, $C_1$) alkyl group, and $Z^-$ is a counter ion.

Any suitable counter ions may be employed, e.g., halide, acetate, carbonate, sulfate, mesylate, maleate, citrate, just to name a few).

In certain embodiments, the molecular assembly is cross-linked both inter-molecularly and intra-molecularly.

In certain embodiments, the molecular assembly is adapted to de-crosslink partially or completely upon contact with a biological or chemical stimulus.

In certain embodiments of the molecular assembly, X comprises a pH-sensitive functional group.

In certain embodiments of the molecular assembly, X comprises a redox-sensitive functional group.

In certain embodiments, each n is independently 1. In certain embodiments, each n is independently an integer from about 2 to about 6 (e.g., 2, 3, 4, 5, 6).

In yet another aspect, the invention generally relates to a method for forming a molecular assembly, comprising: mixing an amphiphilic polymer and a nucleic acid to form a polymer-nucleic acid complex; crosslinking the polymer in the polymer-nucleic acid complex to form a crosslinked polymer network entrapping the nucleic acid therein; and contacting the crosslinked polymer-nucleic acid complex with a zwitterionic lipid and a PEGylated lipid to form a coating on the crosslinked polymer-nucleic acid complex, wherein the coating comprises the zwitterionic lipid and the PEGylated lipid.

In certain embodiments of the method, the crosslinked polymer-nucleic acid complex is adapted to de-crosslink partially or completely upon contact with a biological or chemical stimulus.

In certain embodiments of the method, the crosslinked polymer-nucleic acid complex is adapted to de-crosslink partially or completely upon a stimulus selected from a change in pH or a change in redox potential.

In certain embodiments of the method, the crosslinked polymer-nucleic acid complex is one that is disclosed herein.

In yet another aspect, the invention generally relates to a method for delivering a nucleic acid molecule, comprising: forming a molecular assembly disclosed herein; and directing the molecular assembly to a target site.

In certain embodiments, directing the molecular assembly to a target site comprises administering the molecular assembly to a subject in need thereof thereby releasing the entrapped nucleic acid molecules at the target site.

The following examples are meant to be illustrative of the practice of the invention and not limiting in any way.

Examples

Abbreviations siNC: siRNA-Negative Control; LF: Lipofectamine; PLK1: polo-like kinase-1; MDR1: multi drug resistant-1; CLSM: Confocal Laser Scanning Microscopy.

The self-assembly process was envisioned in three key steps. First, a cationic amphiphilic polymer would be utilized to electrostatically capture the siRNA (Scheme 1, FIG. 1a-b). Note that electrostatic interaction energy is governed by Coulomb's law ($E=q_1 \cdot q_2/4\pi\varepsilon_0\varepsilon r$), where $\varepsilon$ represents the dielectric constant of the medium. In this case, the ionic interaction between the polymer and the siRNA can be significantly enhanced in low dielectric media. The hydrophobic alkyl chain in the amphiphilic random copolymer facilitates the complexation between the polymer and the siRNA in an organic-rich solvent medium, where the electrostatic interactions are expected to be strong. However, the medium is not completely non-aqueous, as polyelectrolyte interactions are entropically driven and it is important to accommodate the critical counterion dissociation that facilitates the interaction between these two macromolecules. (Bucur, et al. 2006 *J. Am. Chem. Soc.* 128 (42), 13690-13691.)

Second, while utilizing the cationic charge to bind the siRNA with high affinity, being able to eliminate the cationic charge in the system is preferred since it has been implicated in many complications in non-viral carriers. (Xue, et al. 2014 *Nanomedicine (London, U. K.)* 9 (2), 295-312.)

Therefore, utilized here a cationic functional group that can be triggered to concurrently self-crosslink and release the cationic functionality (Scheme 1, FIG. 1b-c). Such a process switches the driving force for retaining the siRNA within the assembly, from an electrostatic one to a combination of physical incarceration (due to crosslinking) and solvophobic forces (due to the unfavorable organic-rich medium for the highly charged siRNA). Finally, the resultant complex from this process is relatively apolar with lipophilic alkyl chains on their surface; this complex therefore is not amenable for distribution in aqueous media. This incompatibility is utilized to achieve a hydrophobic force driven coating of charge-neutral lipids in aqueous medium. The concentration of the lipids in this step is such that it does not exhibit self-assembly by itself, but does so on the surface of the existing hydrophobic exterior of the polymer-siRNA complex. This symbiotic self-assembly, where the organization of each of these components into the assembly is dependent on the presence of other components in the system, is thus achieved in three convenient steps.

Synthesis, Characterization and Crosslinking Study of Cationic PDS-Dodecyl Polymer (⊕PPDS/DD)

To achieve the desired self-assembly, a cationic random copolymer PDS-Dodecyl polymer (⊕PPDS/DD) was targeted (FIG. 1a). This copolymer was synthesized via RAFT polymerization of pyridyl disulfide methacrylate and dodecyl methacrylate monomers (molar ratio 9:1, FIG. 1) to obtain p(PDSMA-co-DodecylMA) polymer (PPDS/DD; MW=14.5 kDa; Đ: 1.3). The nitrogens in the PDSMA side-chain were quantitatively methylated using methyl triflate to achieve the ⊕PPDS/DD polymer (FIG. 1). All polymers were characterized with 1H, 13C & 1H-15N NMR, GPC and FT-IR spectroscopy (FIG. 8-12). Methylation of the PPDS/DD polymer was confirmed from the chemical shift and integration of pyridinium ring protons in the final ⊕PPDS/DD polymer.

To further confirm the synthesis of the ⊕PPDS/DD polymer, two-dimensional heteronuclear correlation NMR experiments (1H-15N HMBC, FIG. 10) were performed with the synthesized polymers and 1-methylpyridine-2-thione molecule, released after crosslinking with 1,4-dithiothreitol (DTT, reported in equivalents). A clear shift of 15N NMR band for ⊕PPDS/DD polymer, in addition to appearance of a new correlation band corresponding to methylated nitrogen, confirms successful installation of cationic charge in the ⊕PPDS/DD polymer. Further, 1H NMR spectra for differentially crosslinked samples in presence of different amounts of DTT showed the disappearance of the methylated-PDS units with the concurrent appearance of the peaks that correspond to the small molecule byproduct of the crosslinking reaction, N-methylpyridothione (FIG. 1d). These experiments were carried with the polymer by itself without self-assembling the polymer through electrostatic complexation with siRNA, for characterization purposes. Note that complete crosslinking was achieved at 1 equiv DTT (2 times excess than required) which could be attributed to suppressed reactivity owing to steric barriers.

'Symbiotic Self-Assembly' to Create L-siP Nanoassemblies

The first step of proposed self-assembly (Scheme 1, FIG. 1e) involves electrostatic complexation between ⊕PPDS/DD polymer with naked siRNA in acetone:water mixture (70:30 v/v). In addition to reducing the dielectric constant of the media33 to facilitate greater Coulombic interaction, the choice of solvent mixture is also optimized for the solubility of both ⊕PPDS/DD polymer & siRNA. The amphiphilicity of ⊕PPDS/DD polymer, governed by the ratio of cationic PDS and dodecyl moieties, was also found to affect the solubility of such complexes. It was found that 90:10 ratio polymer exhibited better solubility and complexation capability, compared to that of the initially attempted 70:30 ratio polymer. All subsequent complexation experiments were conducted with the 90:10 ratio polymer in the acetone:water co-solvent system.

To further analyze whether the observed interaction between the polymer and the siRNA is indeed based on electrostatics, molecular dynamics (MD) simulations was conducted using a coarse-grained (CG) molecular model of this system in the acetone:water 70:30 mixture. Simulations show that while the cationic polymers and the oligonucleotides are held together, removal of cationic charge in the polymer detaches the oligonucleotides from the polymer chain. This supports the idea that the self-assembly process is controlled by electrostatic interactions.

The next step in the self-assembly involves structurally reinforcing the complex through a chemical crosslinking reaction, which concurrently also releases the cationic charge from the polymer. This crosslinking step was executed using DTT, where the rapid thiol-disulfide exchange reaction between DTT and the methylated-PDS unit affords a thiol moiety on the polymer side chain, along with a stable small molecule byproduct, viz. N-methylpyridine-2-thione. The thiol moiety on the polymer chain can subsequently react with other methylated-PDS units within the complex to generate crosslinks. Note that this crosslinking step helps to shed positive charge, while also stitching the polymer chains to cage siRNA, thus preventing the loss of siRNA that is electrostatically encapsulated in the first step. More details on the effect of crosslinking density is provided in the next section.

Note that the complexation and crosslinking steps were conducted in an organic rich (acetone-water) media. In order for using this complex to deliver the siRNA molecule to cells, this complex must be in an aqueous media. To achieve this, the complex was coated with lipids in aqueous phase. Since the crosslinked polymer-siRNA complex was achieved in an organic solvent, it was envisaged that the surface of the complex is apolar and would therefore be viable for coating with lipid molecules. Accordingly, a combination of a zwitterionic lipid (1,2-dioleoyl-sn-glycero-3-phosphoethanolamine (18:1 (Δ9-Cis) PE (DOPE)) and a PEGylated lipid (1,2-distearoyl-sn-glycero-3-phosphoethanolamine-N-[methoxy(polyethylene glycol)-2000](ammonium salt, DSPE PEG-2000)) was used, because of their fusogenic and solubilization abilities respectively. (Gallas, et al. 2013 *Chem. Soc. Rev.* 42 (20), 7983-7997; Dominska, et al. 2010 *J. Cell Sci.* 123 (Pt 8), 1183-9; Zhu, et al. 2015 *Proc. Natl. Acad. Sci. U.S.A.* 112 (25), 7779-84.)

Briefly, a mixture of DOPE and DSPE PEG-2000 lipids was initially dissolved in water at a concentration much below their critical aggregation concentrations. (Shi, et al. 2011 *Angew. Chem., Int. Ed.* 50 (31), 7027-31.) The crosslinked polymer-siRNA nanoassembly was then added to the aqueous lipid mixture (water/organic=20, v/v) for the self-assembly of lipids on its surface to produce the final lipid-polymer-siRNA (L-siP) nanoassembly (Scheme 1). Interestingly, the overall self-assembly process is considered symbiotic, because the lipids are used at concentrations well below their CACs and yet it self-assembles on the surface of the polymer-siRNA complex, which in itself required functional complementarity for its formation.

Figure 2:
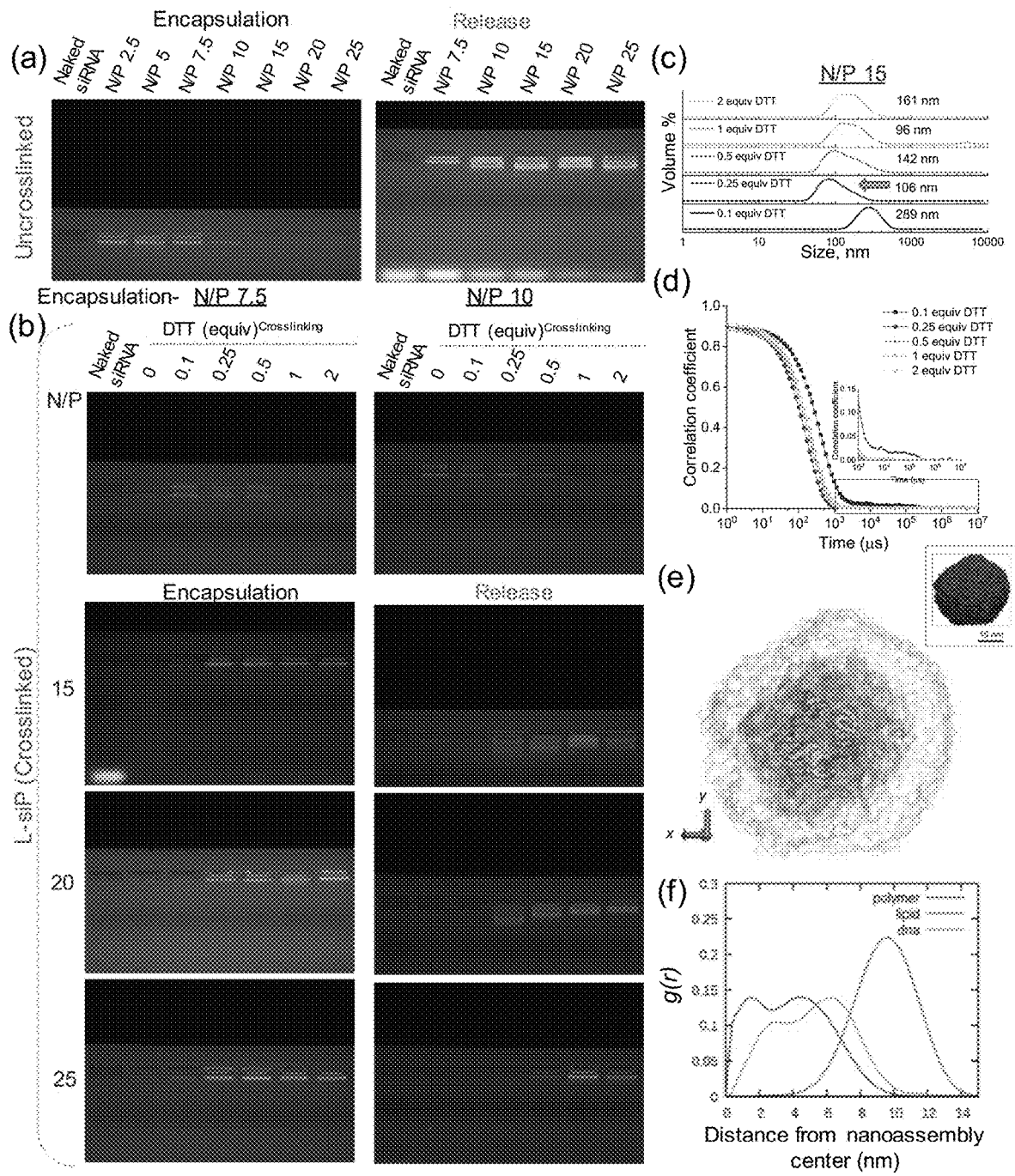
FIG. 2. Effect of N/P ratio & cross-linking on encapsulation stability & siRNA release: (a) Variation of N/P for uncrosslinked particles; (b) Effect of variation of crosslinking measured by the DTT feed amount at higher N/P ratio on encapsulation & siRNA release; (c) DLS size distribution and (d) correlation diagram for N/P 15 nanoassemblies at different cross-linking; (e) Lipid coated nanoassembly constructed with CG-MD simulation: snapshot of the equilibrated L-siP15/1 (cut in half on the major diameter to clearly see the interior). Polymer is shown in transparent green, the dsDNA in yellow and the polymer outer layer is transparent grey (inset: exterior of the NA, where lipids are shown in grey); (f) Radial distribution functions g(r) providing the relative probability to find polymer, dsDNA and lipids at various distances from the center of the nanoassembly.

Effect of NIP and Crosslinking on Complexation and Triggered Release of siRNA from L-siP The relative ratio of complementary charges (N/P) is often used, with number of positively charged nitrogens (N) in the polymer to the number of negatively charged phosphate moieties (P) in the nucleic acid as the measure, to evaluate the complexation efficiency. To understand the effect of this ratio on complexation, the amount of polymer was systematically varied to investigate the construction of L-siP assemblies at different N/P ratios (FIG. 2). All particles were coated with DOPE and PEG-lipids to make them hydrophilic and stable in aqueous medium. The siRNA encapsulation was evaluated with agarose gel retardation assay (FIG. 2a-b).

Figure 13:
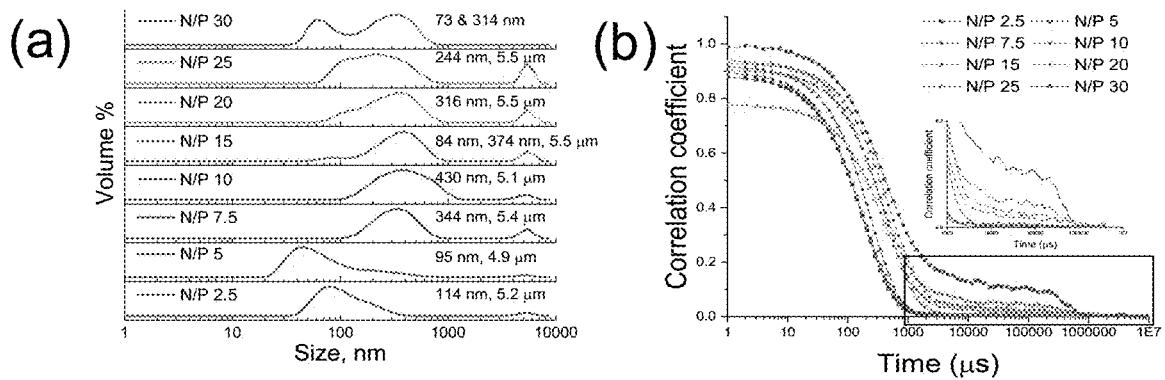
FIG. 13. DLS size distribution (a) and correlation diagram (b) of uncrosslinked particles at different N/P ratios.

First, complexation was studied at different N/P ratios without any crosslinking. At low polymer concentrations (N/P of 2.5 and 5), the complexation was found to be inefficient as noted from the significant presence of free siRNA in the gel. At N/P 7.5 and above, the siRNA encapsulation was found to be efficient (FIG. 2a). In addition to the encapsulation efficiency, it is also necessary to release the encapsulated siRNA molecules in the presence of a biologically relevant intracellular trigger. (Dutta, et al. 2017 *J. Am. Chem. Soc.* 139 (16), 5676-5679; Ghosh, et al. 2006 *Macromolecules* 39 (17), 5595-5597.) Therefore, the release of siRNA from these assemblies were assessed in the presence of a redox-stimulus at a concentration that is similar to that found in the cytosol (10 mM glutathione, GSH). In the presence of this stimulus, the siRNA release was found to be significant in the N/P 7.5 complex, but was significantly lower at higher N/P ratios (FIG. 2a). However, dynamic light scattering (DLS) measurements revealed non-uniform, bimodal and broad particle size distributions with poor correlation coefficients for all uncrosslinked nanoassemblies (FIG. 13a-b) indicating unstable nanoparticle formations.

Figure 14:
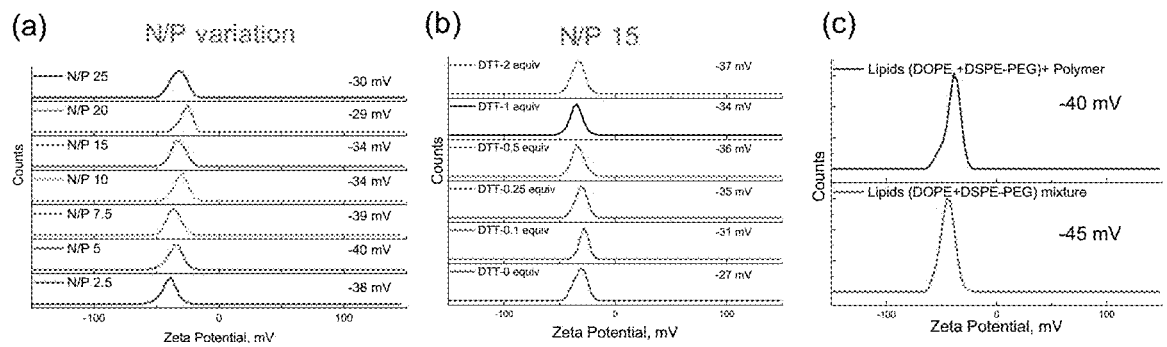
FIG. 14. Zeta potential measurements for (a) uncrosslinked samples at different N/P ratios; (b) for L-siP$^{15/1}$ with varying crosslinking; (c) lipids and mixture of (lipids+$\oplus P^{PDS/DD}$). At higher N/P ratio and crosslinking density zeta potential decrease upto ~10 mV. Note that the zeta potential is not expected to show a significant change as the lipid layers are surrounding the particles in all cases which shows negative zeta potentials (see FIG. S7c).

The study of uncrosslinked complexes above provides an initial insight into the optimal N/P ratios. Note however that in the final complex, the positive charges will be removed through crosslinking. Therefore, the efficiency of siRNA encapsulation in this scenario might be very different as the balance between weakening of the complexation due to charge removal and strengthening the incarceration due to crosslinking would play an important role. To evaluate this balance, the effect of crosslinking towards the formation of L-siP particles at different N/P ratios are studied (FIG. 2b). Upon increasing crosslinking degree, leakage of siRNA was evident from the assemblies formed at N/P 7.5 and 10. At higher N/P ratios (starting from N/P 15), in combination with higher crosslinking (0.25 equiv DTT onwards), the siRNA encapsulation was found to be stable (FIG. 2b), as evident from narrow particle size distributions with excellent correlation coefficients. However, the release of siRNA was found to be crosslinking dependent, where the maximum release was obtained between 0.25-1 equiv of DTT crosslinking. This can be attributed to the critical balance of positive charge and crosslinking degree in L-siP nanoassemblies. At lower crosslinking degree (0-0.1 equiv DTT), residual cationic charge left after DTT treatment becomes the dominating factor and is able to hold back the siRNA tightly in the nanoassemblies. While at higher crosslinking degree (2 equiv DTT), siRNAs might be deeply buried and shielded inside the nanoassembly preventing adequate exposure to external reducing release environment. Evidently, at even higher N/P 25, where the polymeric burden was more, negligible release of siRNA was observed for similar reasons (FIG. 2b). Based on these observations, a threshold of N/P 15 was thus considered as an efficient L-siP system for both siRNA encapsulation and release (also see later for quantification). As L-siP nanoassemblies contain lipids, the zeta potential values were found to be negative (−30 to −40 mV, FIG. 14) as an effect of efficient coating of DOPE and PEG-lipids. (Garbuzenko, et al. 2005 *Langmuir* 21 (6), 2560-2568; Meyer, et al. 1998 *J. Cell Biol.* 273 (25), 15621-15627.)

Figure 15:
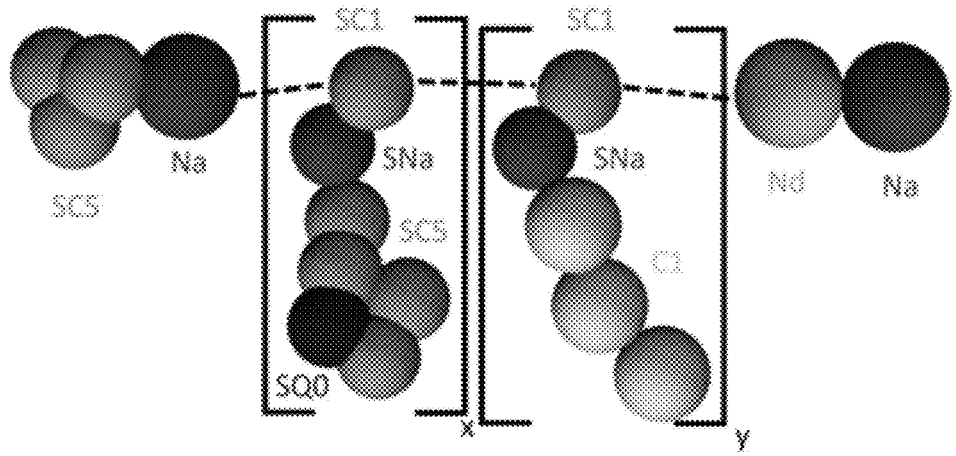
FIG. 15. Coarse grained (CG) representation of the cationic-PDS-Dodecyl polymer ($\oplus P^{PDS/DD}$). The CG MARTINI beads used in the model are indicated in the FIG. SQ0 beads are charged (+1e). When modelling crosslinking, (i) the interaction of the first SC5 bead of the PDSMA chain with DTT has been artificially augmented to observe the spontaneous formation of stable (not breakable) bonds, and (ii) the side groups coordinated to DTT have been then detached from the rest of the polymer.
Figure 16:
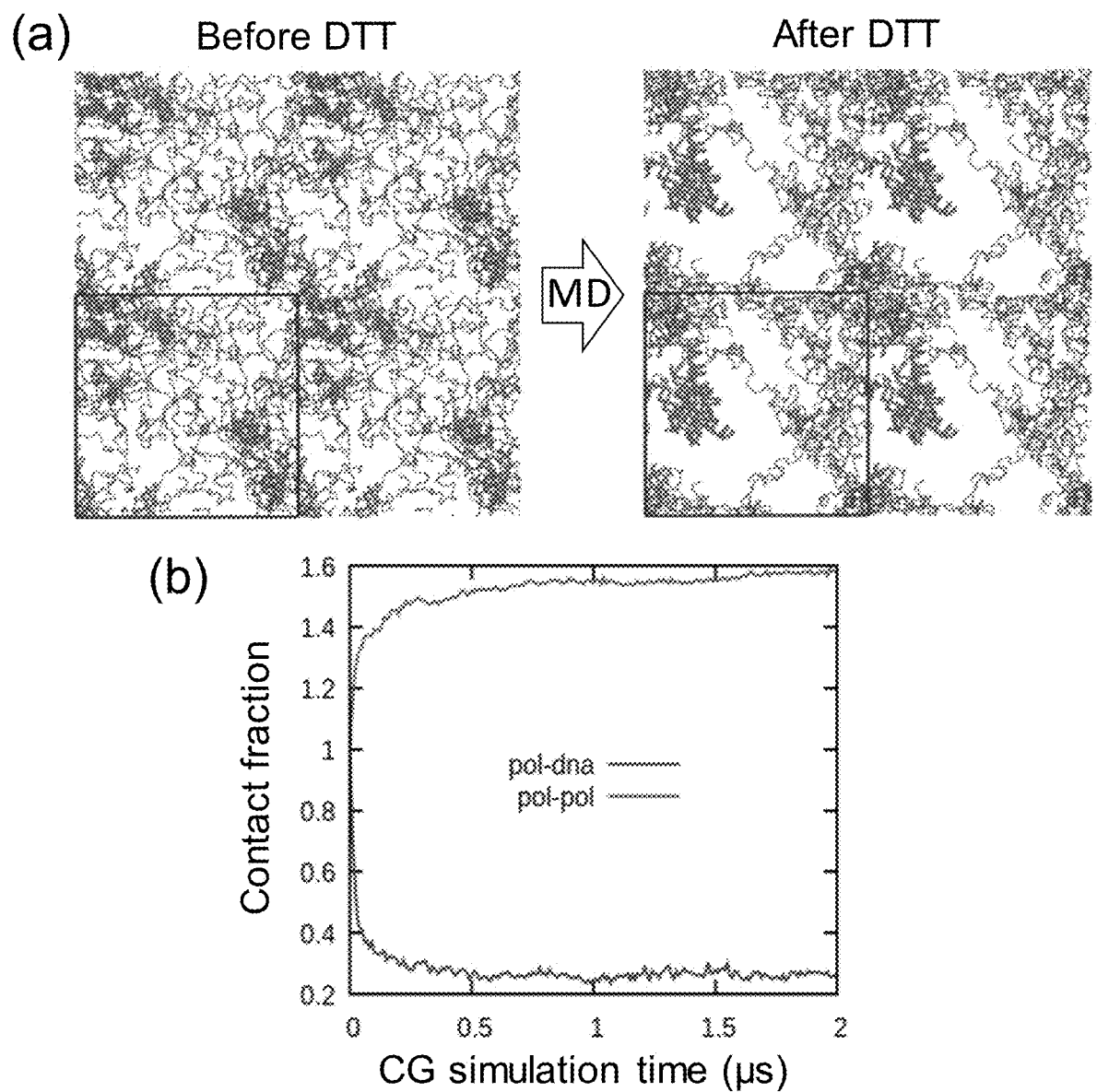
FIG. 16. CG-MD simulations at N/P 7.5 ratio showing the leakage of oligonuclueotides from the polymers following to crosslinking (insertion of DTT molecules). (a) The self-assembled system before DTT insertion appears as a quite loose network, kept together mainly by electrostatic interactions. When DTT crosslinking happens, polymers undergo compaction and the guest nucleotides detach form the polymer chains due to the loss of electrostatic interactions. (b) Quantification of the leakage: number of polymer-polymer and polymer-dsDNA contacts as a function of the CG-MD simulation time after the insertion of DTT.

To further understand the complexation and release process, CG-MD simulations were carried out (FIG. 15). To mimic the crosslinking process, —SS— groups in the polymer assembly were introduced, while cleaving the positively charged functionalities, assuming that crosslinking has occurred. When the crosslinking was introduced in the equilibrated N/P 7.5 model system, leakage of the oligos from the polymer (FIG. 16) was clearly observed. Next, a molecular model was built for the more promising N/P 15 L-siP system (FIGS. 2d and 2e). An N/P 15 polymer-oligo network was spontaneously formed in 70:30 acetone:water (v/v) via CG-MD simulation. Then, a 100% crosslinking was introduced by adding a suitable number of DTT molecules in the system. To be sure to form a single aggregate in the center of the simulation box (useful for successful steps) following compaction due to crosslinking, a recently optimized simulation technique was used that push the system toward a single aggregation center. (Bochicchio, et al. 2017 *J. Phys. Chem. Lett.* 8 (16), 3813-3819.) The DTT molecules selectively and strongly interacted with the —SS— groups in the polymer during this CG-MD simulation, while after coordination the cationic groups of the polymer involved in the process have been cleaved. Next, DOPE lipid molecules was added and the solvent was replaced consistently with the experiments (water/organic=20, v/v). Then, the L-siP model nanoparticle was equilibrated via CG-MD simulation, which provided us with an insight into the structure of this assembly at a resolution <5 Å (FIG. 2d). The lipid layer (transparent grey) covers the interior of the assembly, where the oligos (yellow) appear as trapped in the polymer matrix (green). The radial distribution functions of the polymer were computed from the equilibrated phase CG-MD trajectory, lipid and oligonucleotides (g(r): relative probability to find these in space) as a function of the distance from the center of the nanoparticle (FIG. 2e). The superposition of the cyan and purple curves in FIG. 2e indicates that the polymer and the oligos are uniformly mixed in the core of the assembly while the lipids cover it and constitute the shell of the nanoassembly, which resulted well stable L-siP in such experimental conditions.

Figure 3:
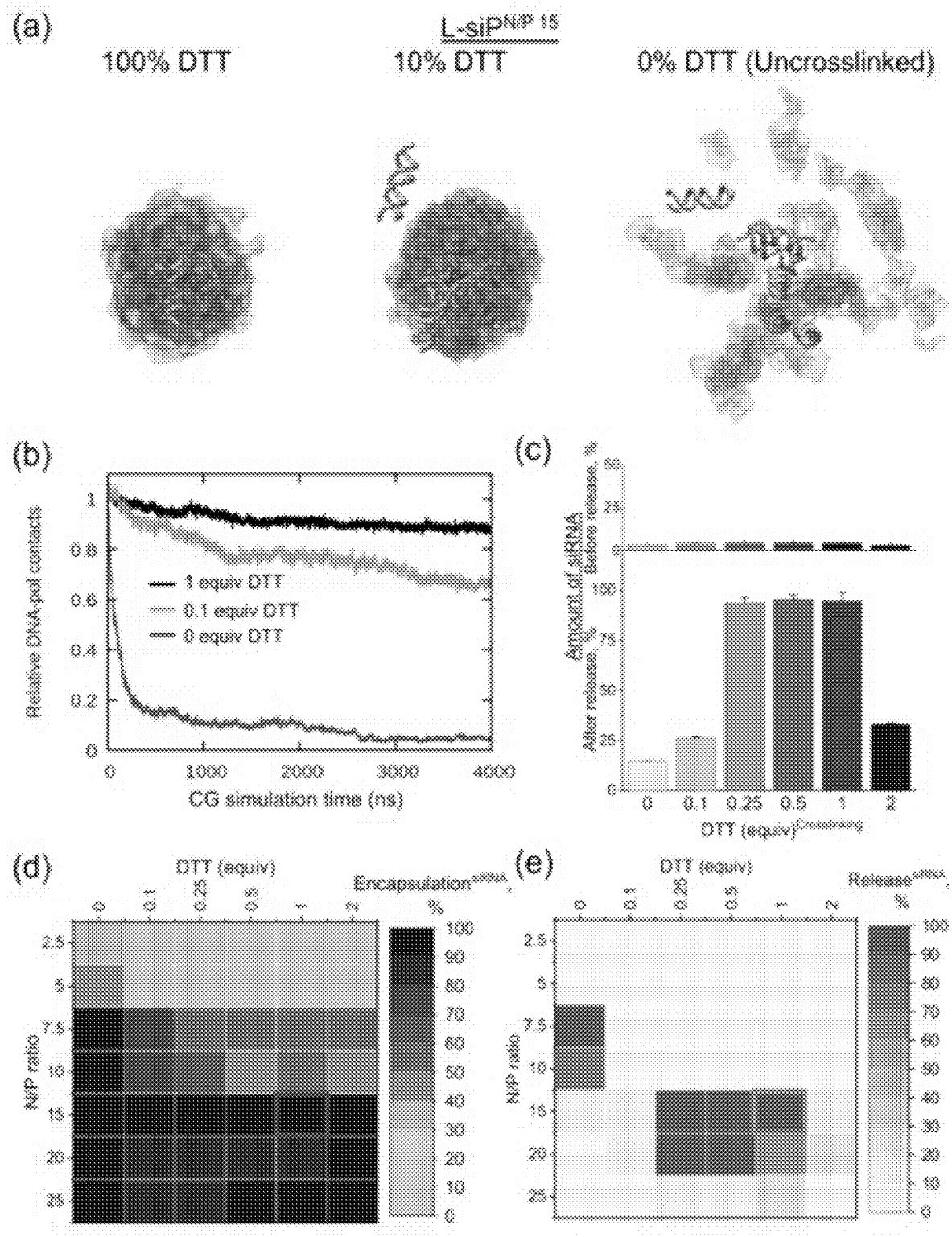
FIG. 3. (a) CG-MD simulation snapshots (taken after 4 µs) showing how the oligo release proceeds at different degrees of de-crosslinking: no decrosslinking, 90% of crosslinking removed and complete de-crosslinking; (b) Quantification of the different release behaviors as the number of contacts between oligo and polymer as a function of simulation time (initial number of contacts normalized to 1); (c) Ribogreen assay to quantify encapsulated & released siRNA from L-siP15/1; Summary of encapsulation (d) and release profiles (e) at different N/P & crosslinking ratios showing the most promising composition to be N/P 15 at 1 equiv DTT crosslinking.

Starting from this equilibrated crosslinked L-siP model, the nanoassembly was further probed to understand the effect of crosslinking on stabilization and release of oligonucleotides. Upon deleting the lipid shell, the release of encapsulated oligonucleotides as a function of the de-crosslinking ratio was studied. The polymer-oligo complex remains stable in 100% DTT, i.e., fully crosslinked condition (FIG. 3a). However, at 90% de-crosslinking (90% of DTT molecules eliminated from the model) partial release of oligoes from the assembly was observed, which completely disassembled under complete removal of DTT (0% DTT). FIG. 3b quantifies these observations, showing the number of contacts between the polymer and the guest oligos over time calculated with respect to the initially equilibrated nanoassembly.

The encapsulation and release of siRNA from the L-siP nanoparticle via RiboGreen assay for the promising N/P 15 case was further experimentally confirmed (FIG. 3c). (Buyens, et al. 2008 *J. Control Release* 126 (1), 67-76.) Under the encapsulated state, siRNA is significantly inaccessible to the assay reagent showing no apparent fluorescence signal generation. However, the amount of siRNA, once released from the assembly under reducing conditions, the fluorescent signal generation was found to be dependent on the crosslink density. These observations further support the results obtained from the agarose gel retardation study above (FIG. 2a-b). The degree of siRNA encapsulation and release obtained from agarose gel studies is summarized in FIGS. 3d and 3e.

Figure 17:
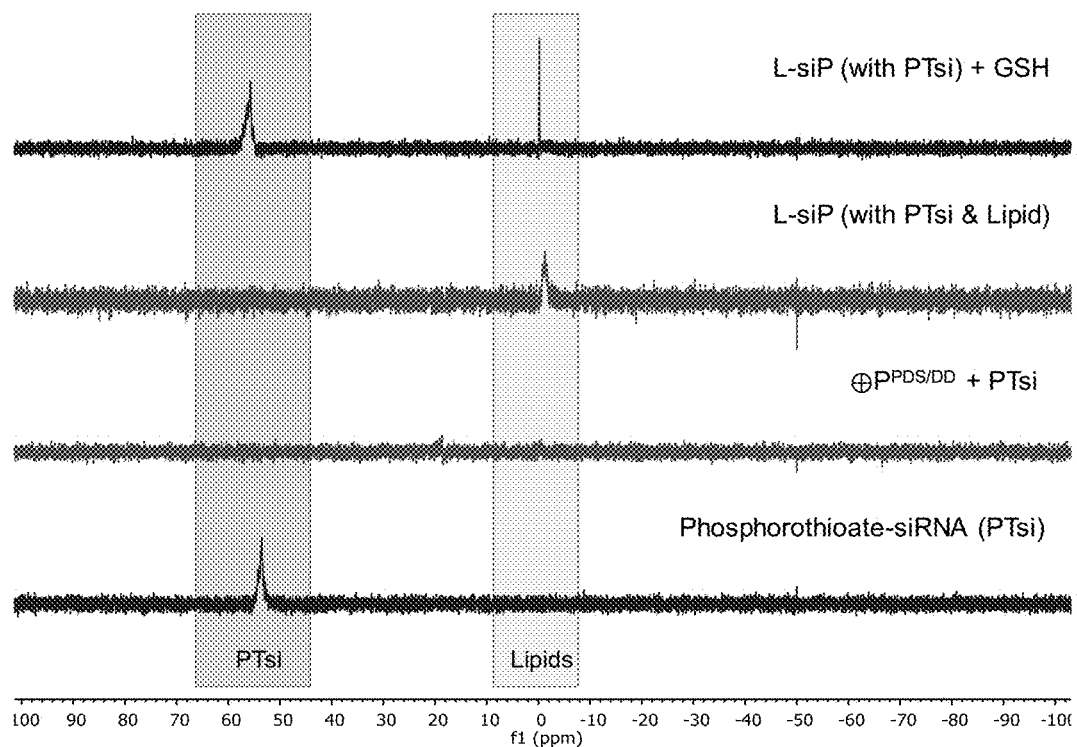
FIG. 17. $^{31}$P NMR spectra indicating peaks from phosphorothioate-siRNA (PTsi, δ53.56-55.97 ppm) and lipids (δ~0 ppm). For crosslinked $\oplus P^{PDS/DD}$+ PTsi and final L-siP (with PTsi & Lipid) samples, no $^{31}$P peak from siRNA is observed due to complexation, whereas peak from lipid coating is visible. Once PTsi is released from L-siP nanoassembly, it becomes visible again in $^{31}$P NMR.
Figure 18:
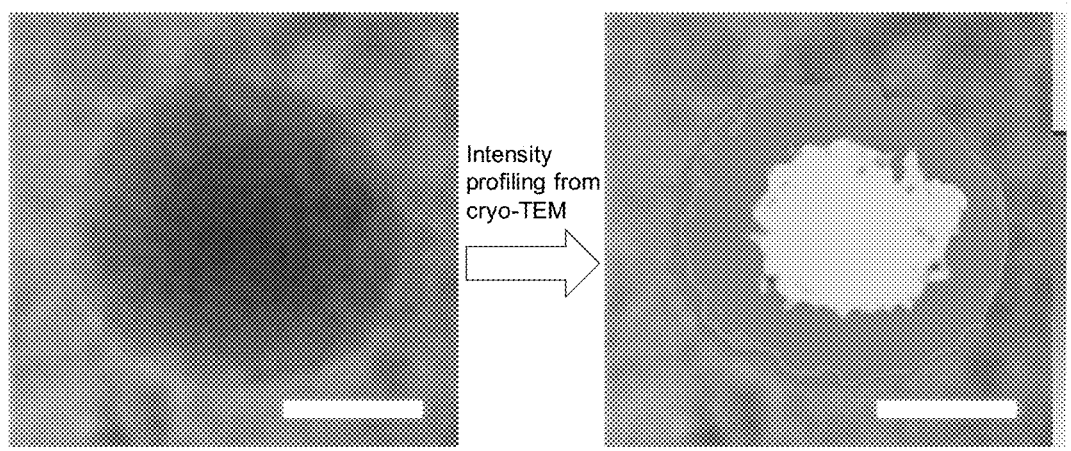
FIG. 18. Color-coded intensity profiling of a single L-siP$^{15/1}$ nanoassembly showing a dense crosslinked polymer core with relatively light external lipid coating, scale: 50 nm.

To further understand the fate of siRNA during encapsulation and release steps, 31P NMR experiments were performed to monitor the processes (FIG. 17). A phosphorothioate-modified siRNA (PTsi, δ~53 ppm) is utilized to distinguish it from the phosphorus in phosphate groups of DOPE and DSPE-PEG lipids (δ~0 ppm). (Leung, et al. 2012 *J. Phys. Chem. C* 116 (41), 22104-22104; Viger-Gravel, et al. 2018 *J. Phys. Chem. B* 122 (7), 2073-2081.) Once encapsulated the mobility of the siRNA inside the polymer cage will be significantly impaired compared to its situation in bulk solvent. As a result, the 31P band at δ~54 ppm (for PTsi) is completely eliminated after the formation of L-siP nanoassembly, whereas it reappears upon subjecting it with the release condition (with 10 mM GSH & Triton X-100, FIG. 17).43 This evidence further supports the results obtained from agarose gel retardation and RiboGreen assay studies (FIG. 2a-b, 3c). Evidently, to reduce the quantity of polymer in the L-siP assembly construction with suitable high crosslinking degree (in context of reducing cytotoxicity by shedding cationic charge), the L-siP assembly (L-siP15/1) constructed under N/P 15 with crosslinking using 1 equiv of DTT (excess DTT was choosen to ensure complete removal of cationic charge as discussed in FIG. 1d) was chosen as the desired candidate for further cellular experiments.

Figure 4:
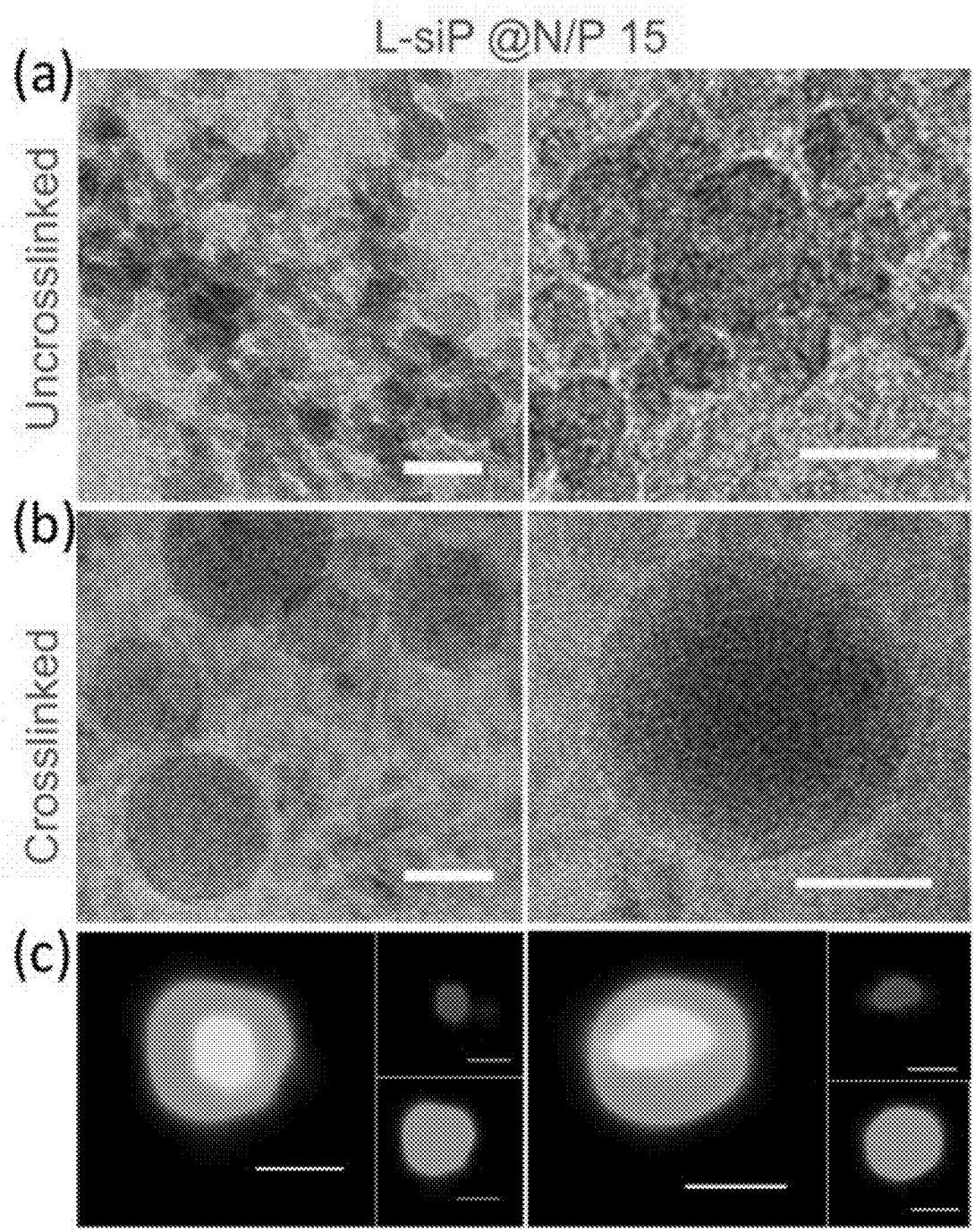
FIG. 4. Cryo-TEM images of L-siP particles at N/P 15 (a) without crosslinking & (b) with cross-linking (DTT-1 equiv), scale: 50 nm; (c) N-STORM confocal microscopy images of single L-siP15/1 particle, red: cy3-siRNA, green: carboxyfluorescein labelled DSPE-PEG lipid that coats the polymer-siRNA nanoassembly, scale: 100 nm.

Prior to evaluating the intracellular delivery of siRNA using these nanoassemblies, the nanoassemblies via cryo-TEM and N-STORM confocal fluorescence microscopy (FIG. 4) was further characterized. Cryo-TEM studies were performed for both the N/P 15 uncrosslinked and crosslinked samples. Images of the uncrosslinked assembly (FIG. 4a) clearly show a fractal morphology consisting loose aggregates, whereas crosslinked L-siP15/1 nanoassembly (FIG. 4b, S11) showed uniform spherical assemblies with an average size of ~100 nm. These results are in accordance with earlier DLS observations (FIG. 2b-c, S6). To further characterize the particle construction, L-siP15/1 nanoassembly was prepared utilizing carboxy-fluorescein labelled DSPE PEG-2000 lipid and cy3-labelled siRNA. As per the symbiotic self-assembly approach, polymer complexed siRNA would dwell in the inner core while the shell would comprise lipid mixture surrounding the electrostatic polymer-siRNA complex. The N-STORM images in FIG. 4c clearly demonstrate the L-siP nanoassembly design with red cy3-siRNA comprising the inner part and green lipid layer encapsulating it externally. Interestingly, color-coded intensity profile defined by the electron scattering cross-section across the particles also matches the N-STORM measurements (FIG. 4c & S11).

Cellular Uptake and Intracellular Distribution

Figure 5:
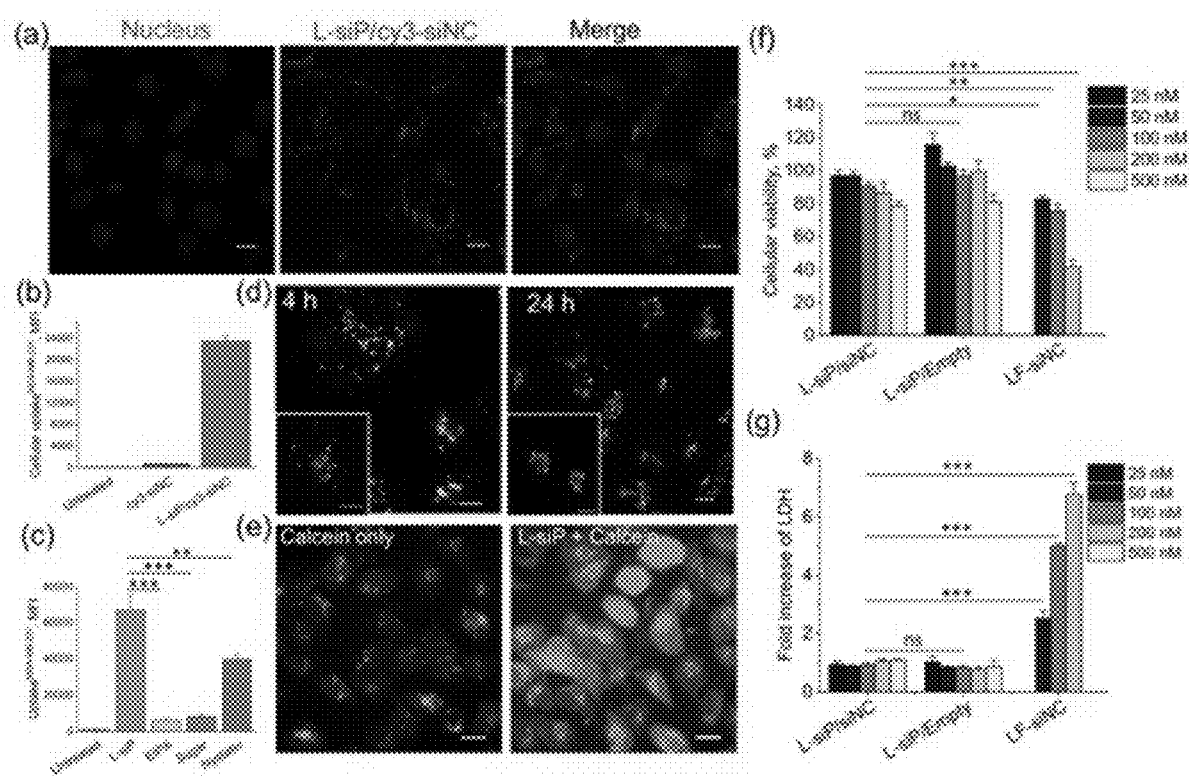
FIG. 5. siRNA delivery in MDA-MB-231 cell line: (a) Cellular uptake of cy3-labelled siRNA (4 h incubation), scale: 20 µm; (b) Quantification of uptake with flow cytometry (4 h incubation); (c) Mechanism of siRNA transfection in presence and absence of endocytic inhibitors; (d) Endosomal colocalization of red cy3-siRNA and Lysotracker blue (pseudo-colored as green) after 4 h and escape after 24 h incubation, scale: 20 µm; (e) Calcein assay showing efficient escape of calcein from endosome and localization in cytosol in presence of L-siP15/1 NA, scale: 10 µm; (f) Cellular viability and (g) LDH cytotoxicity assay at different L-siP/siRNA concentrations compared to Lipofectamine (LF); Student's t-test: *p<0.001, p<0.01, *p<0.05, ns (non-significant)>0.05.
Figure 19:
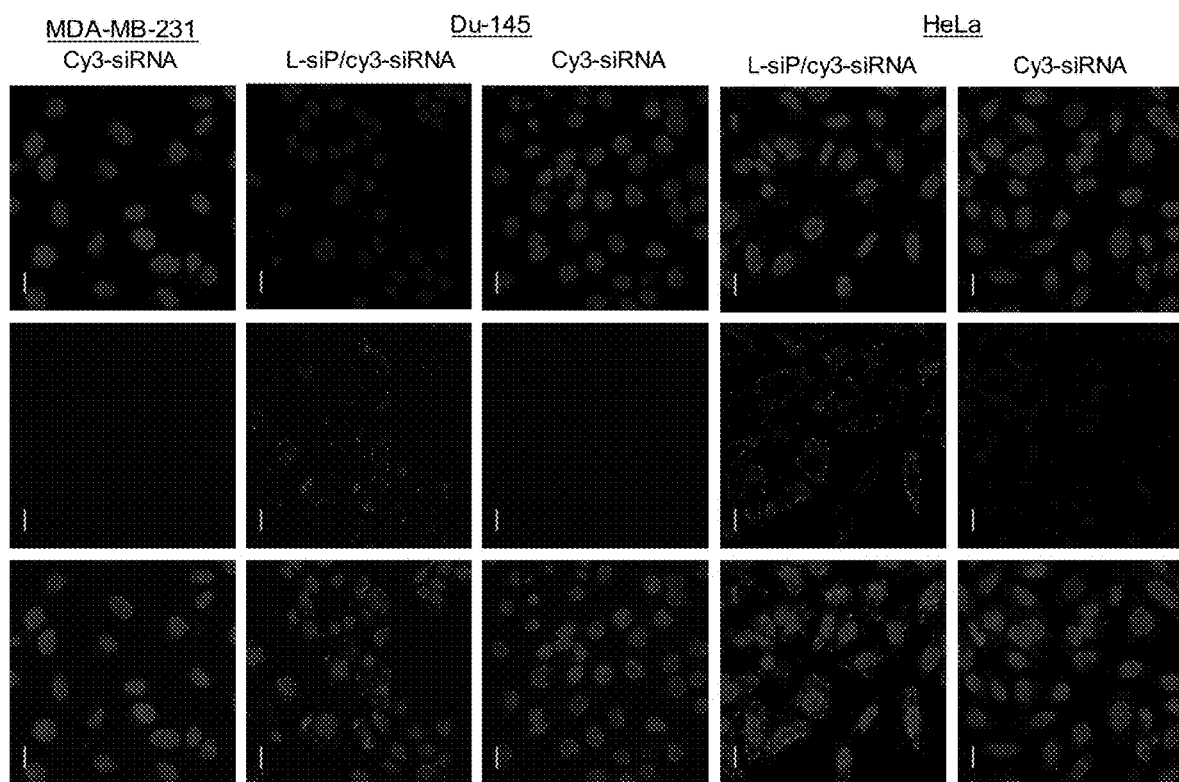
FIG. 19. Cellular uptake of cy3-labelled siRNA in HeLa, DU-145 and MDA-MB-231 cell lines, scale: 20 µm.
Figure 20:
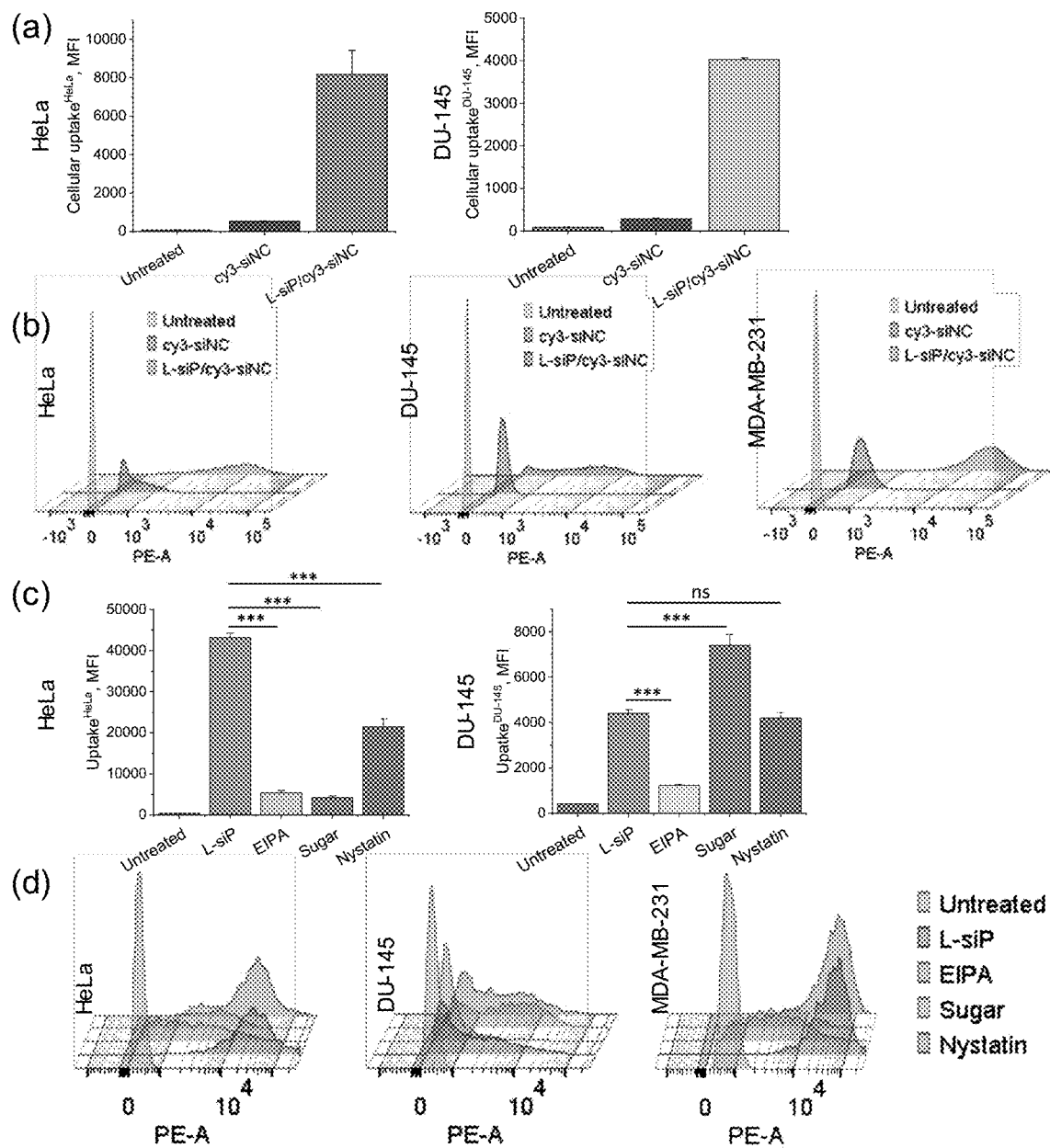
FIG. 20. Quantification of cellular uptake and mechanism of siRNA transfection in presence and absence of endocytic inhibitors for Hela, DU-145 and MDA-MB-231 cell lines through flow cytometry (a, c: bar graph; b, d: histogram plots).

To test the ability of L-siP15/1 towards intracellular delivery of siRNA, these nanoassemblies were prepared using cy3-labelled siRNA and investigated their cellular distribution in three different cancer cell lines, viz. mammary gland/breast cancer cell line MDA-MB-231, cervical cancer cell line HeLa and a prostate cancer cell line DU-145 (FIG. 5, for MDA-MB-231 and FIG. 19 and FIG. 20 for HeLa & DU-145). As shown in FIG. 5a, a clear distribution of red fluorescence in the cytosolic region confirms efficient transfection of cy3-siRNA nanoassembly (FIG. 5b for flow cytometry quantification). The transfection efficacy was also evaluated in HeLa and DU-145 cells though confocal laser scanning microscopy (CLSM) (FIG. 19) and flow cytometry (FIG. 20). A quantitative comparison reveals the following order of uptake potency in different cell lines: MDA-MB-231>HeLa>DU-145.

Next, the cellular uptake mechanism was probed via utilizing different inhibitors for endocytic pathways in the above-mentioned cell lines through flow cytometry with cy3-siRNA containing L-siP15/1 nanoassembly (FIG. 5c & FIG. 20). EIPA and hyperosmolar sucrose, inhibitors for macropinocytosis and clathrin-dependent endocytosis, respectively were found to have a striking effect on uptake in MDA-MB-231 and HeLa cells, whereas the effect of nystatin, an inhibitor for caveolae-mediated endocytosis, was found to be comparatively reduced. (Majumder, et al. 2018 *Angew. Chem., Int. Ed.* 57 (46), 15040-15044; Chen, et al. 2011 *Blood* 117 (23), 6392-403; Koivusalo, et al. 2010 *J. Cell Biol.* 188 (4), 547-63.)

These results show that the major cellular internalization proceed through macropinocytosis and clathrin-dependent pathways for MDA-MB-231 and HeLa cell lines. In contrary, DU-145 cells only showed a significant decrease in fluorescence intensity when incubated in presence of EIPA indicating macropinocytosis being the exclusive choice of uptake pathway (FIG. 20).

To evaluate the intracellular distribution of delivered cy3-siRNA through L-siP15/1 assembly over time, CLSM of MDA-MB-231 cells was performed in presence of endo/lysosomal stain, lysotracker blue (pseudo-colored in green in FIG. 5d). After 4 hours of incubation, the red fluorescence from cy3-siRNA was observed to be co-localized with lysotracker blue (FIG. 5d), indicating that the nanoassemblies are located in endo/lysosomal compartments. Interestingly, this co-localization diminishes significantly after 24 h incubation, as indicated by clear separation of red (cy3-siRNA) and blue (pseudo-colored in green for lysotracker stain) channels indicating endosomal disruption and release of siRNA into the cytosol. A quantitative comparison is reflected in the decrease in co-localization ratio from 0.65 (4 h) to a lower value 0.34 (24 h). The probable reason for such facile intracellular release of siRNA cargo could be explained from the fusogenicity of DOPE lipid, employed in decorating the L-siP nanoassembly, through attachment and fusion with anionic endosomal membrane.7

Figure 21:
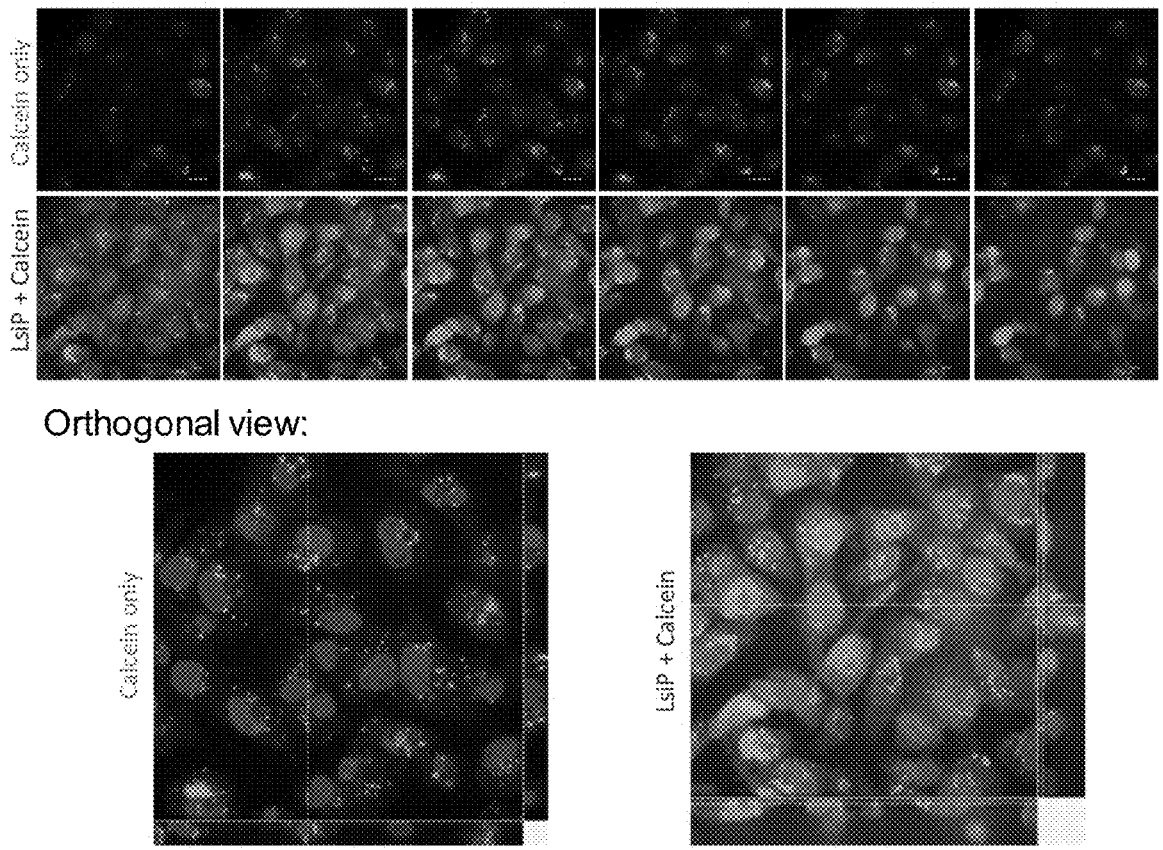
FIG. 21. Calcein assay for MDA-MB-231 cells: z projection (with 2 µm increment) and orthogonal view, scale: 20 µm.

To further investigate whether endosomal disruption is indeed facilitated by L-siP nanoassemblies, calcein green assay (FIG. 5e and FIG. 21) was performed. Calcein, a membrane-impermeable dye, shows punctate green fluorescence above its self-quenching concentration when entrapped in endo-lysosomal compartments. (Ren, et al. 2016 Nat. Commun. 7, 13580.) However, the green fluorescence changes to a bright diffused pattern (dequenched state), if calcein can be released in cytosol after successful escape from endosomes mediated by delivery agents. As shown in FIG. 5e & S14, the punctate green fluorescence of calcein in control cells confirms the endosomal entrapment, whereas a diffused fluorescence is observed for L-siP15/1 nanoassembly treated cells, indicating efficient endosomolytic activity of the L-siP assemblies.

Evaluation of Cytotoxicity and Nuclease Stability for L-siP15/1

Figure 22:
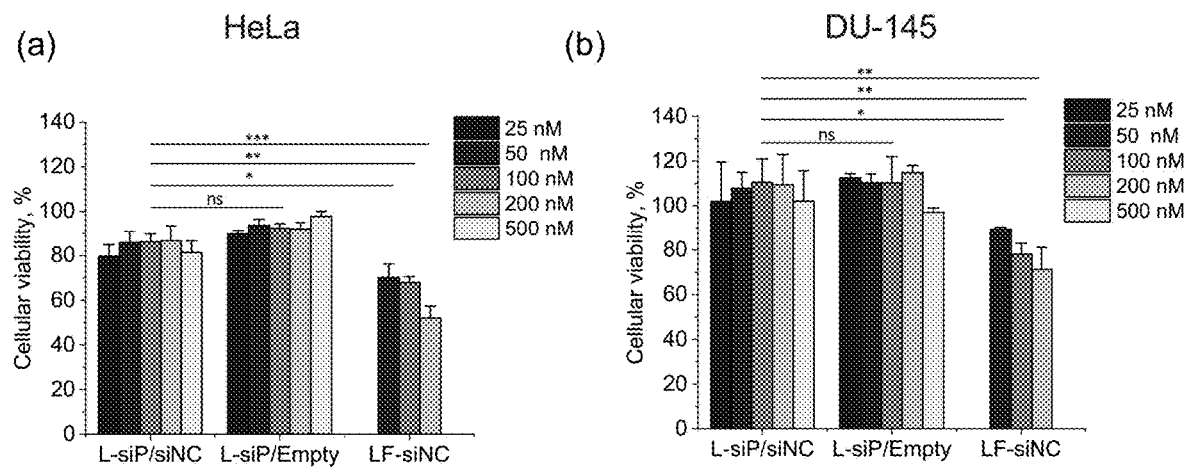
FIG. 22. Cellular viability of (a) HeLa and (b) DU-145 cells in presence of L-siP nanoassembly at different loaded concentrations of siRNA; L-siP/Empty: crosslinked nanoassembly without siRNA (with same polymer concentrations as in L-siP/siNC); siNC: negative control siRNA; LF: Lipofectamine; Student's t-test: *p<0.001, p<0.01, *p<0.05, ns (non-significant)>0.05.
Figure 23:
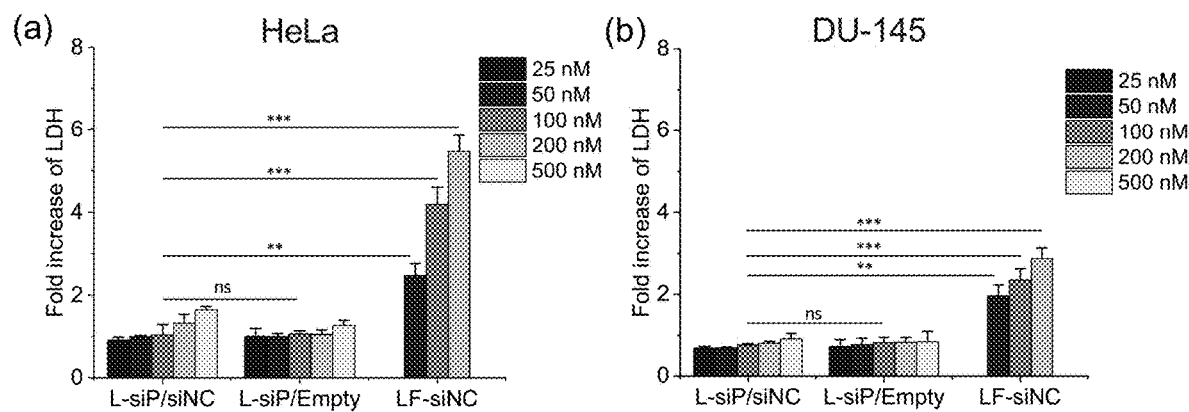
FIG. 23. Cytotoxicity measured by LDH assay in (a) HeLa and (b) DU-145 cells in presence of L-siP nanoassembly at different loaded concentrations of siRNA; L-siP/Empty: crosslinked nanoassembly without siRNA (with same polymer concentrations as in L-siP/siNC); siNC: negative control siRNA; LF: Lipofectamine; Student's t-test: *p<0.001, p<0.01, *p<0.05, ns (non-significant)>0.05.

Stability of the siRNA-polyion based electrostatic complex is mostly guided by the overall high cationic charge which eventually compromises the safety of the delivery agent increasing cytotoxicity. To evaluate the safety feature of L-siP15/1 nanoassembly, cellular viability and plasma membrane integrity in MDA-MB-231 was evaluated (FIG. 5f-g), HeLa and DU-145 (FIG. 22) cell lines. L-siP/siNC nanoassembly (siNC: negative control siRNA) showed ~86% cellular viability even at 200 nM siRNA concentration (with comparable polymer amount for N/P 15), whereas viability reduces to ~42% for lipofectamine-siRNA sample (LF-siNC) at an identical concentration (FIG. 5e). Cytotoxicity study in HeLa and DU-145 cells also demonstrate a high cellular viability compared to lipofectamine (FIG. 22).

Next, the integrity of the plasma membrane through lactate dehydrogenase (LDH) assay was studied. (Zeller, et al. 2015 Chem. Biol. 22 (1), 50-62; Convertine, et al. 2009 J. Control Release 133 (3), 221-9.) The compromised cell membrane would release cytosolic LDH enzyme into cell culture media which, in turn, can be quantified through an absorbance-based assay. 49-50 FIG. 5g shows a minimal to no membrane damage mediated by L-siP assemblies even at a significantly high dosage (200 or 500 nM siRNA). In comparison, LF-siNC samples showed ~3 to 7-fold increase in membrane damage compared to untreated cells (FIG. 5g and S16). These results demonstrate significantly less cytotoxicity of the designed L-siP nanoassembly desirable for a safe delivery agent.

One of the bottlenecks of RNAi based technology is the limited stability of naked siRNA with a plasma half-life of <10 min due to the degradation mediated by serum endonucleases. (Shi, et al. 2013 J. Histochem. Cytochem. 61 (6), 407-420.) Thus, a critical requirement for an efficient delivery agent is to provide end-to-end protection till the cargo is delivered in the intracellular space. To this goal, the stability of the encapsulated siRNA in the presence of RNase A and 10% fetal bovine serum was investigated. (Jafari, et al. 2014 PLoS One 9 (5), e97797; Wang, et al. 2014 Chem. Commun. 50 (58), 7806-7809.)

Figure 24:
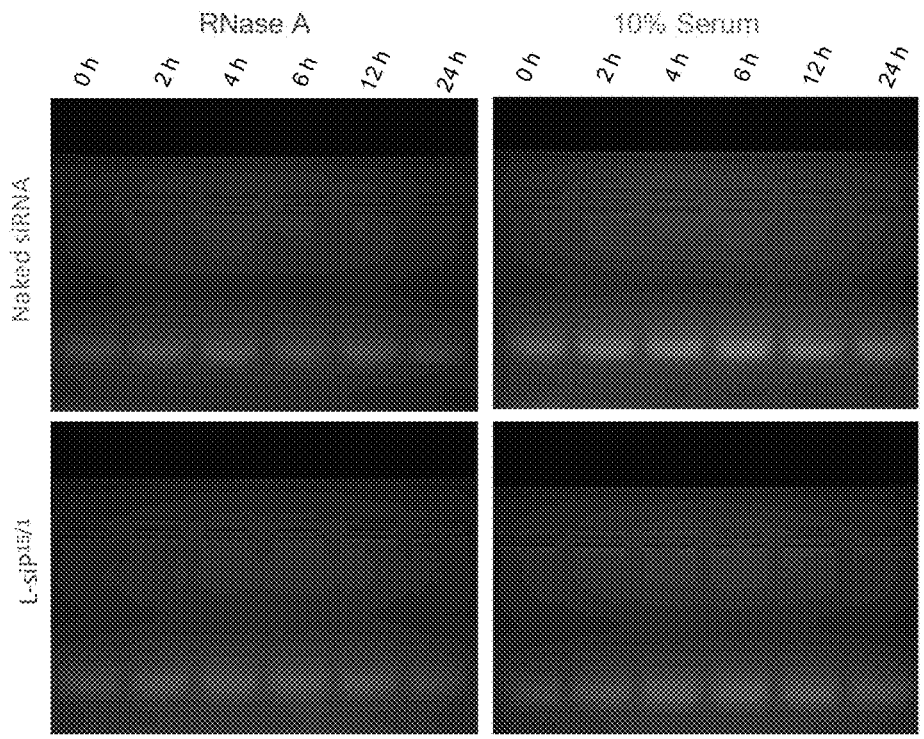
FIG. 24. Stability assessment of siRNA (Naked or L-siP$^{15/1}$) in presence of RNase A and 10% Serum at 37° C.
Figure 25:
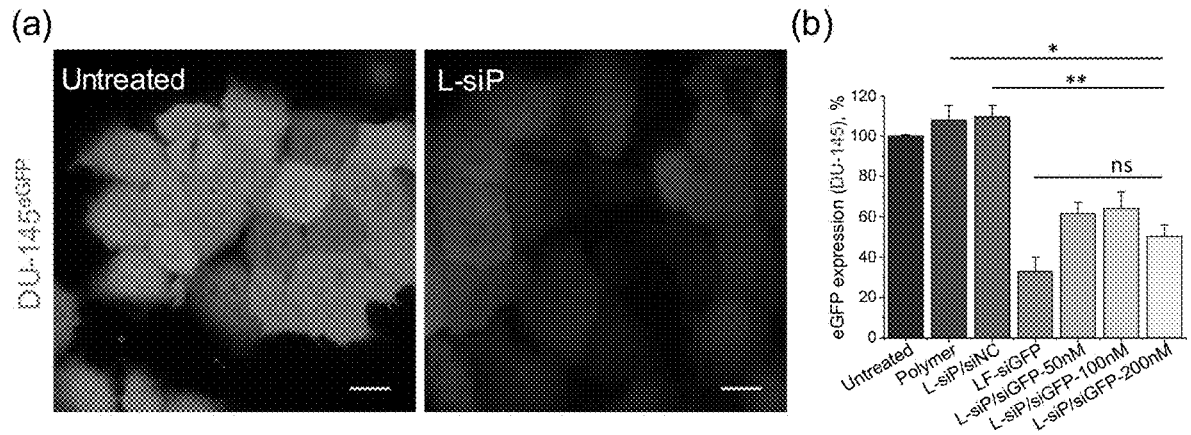
FIG. 25. eGFP silencing with L-siP$^{15/1}$ in DU-145$^{eGFP}$ cells: (a) Confocal microscopy images and (b) flow cytometry data for quantification of eGFP fluorescence, respectively; scale: 20 µm; Student's t-test: *p<0.001, p<0.01, *p<0.05, ns (non-significant)>0.05.
Figure 26:
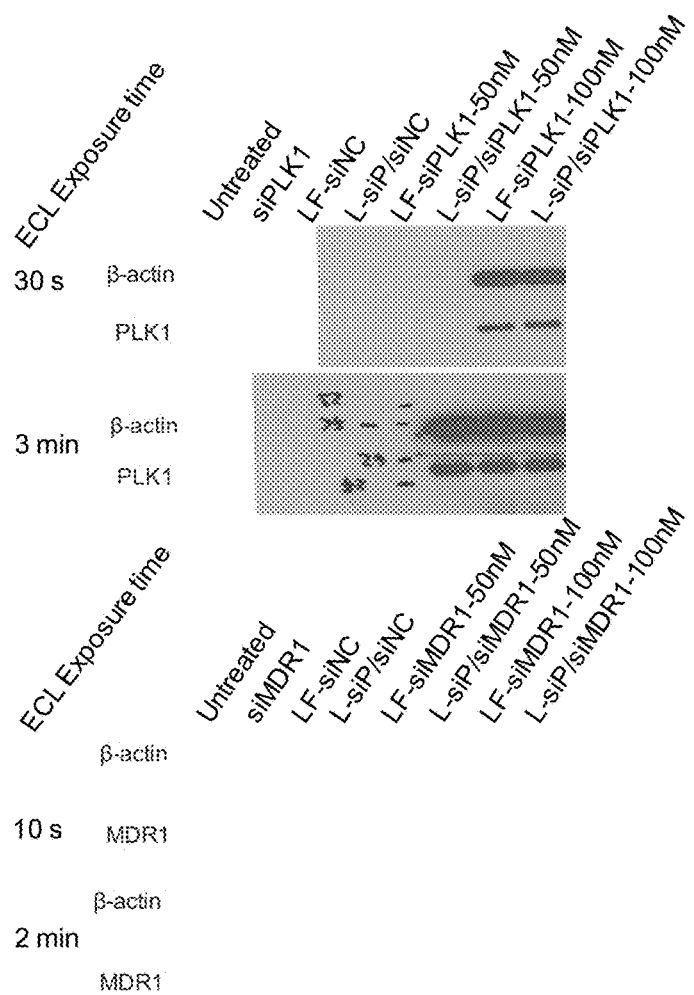
FIG. 26. Western blot analysis for gene silencing: ECL exposure time variation to capture comparative protein expressions.

After incubation at different time interval with RNase A and serum, the L-siP/siNC nanoassemblies were subjected to redox-triggered release condition (10 mM GSH) and evaluated in agarose gel retardation assay. As shown in FIG. 24, L-siP nanoassembly is efficient in protecting siRNA even after 24 h of incubation, whereas the unprotected naked siRNA is completely degraded within 4 h of incubation in presence of RNase A and serum.

Figure 6:
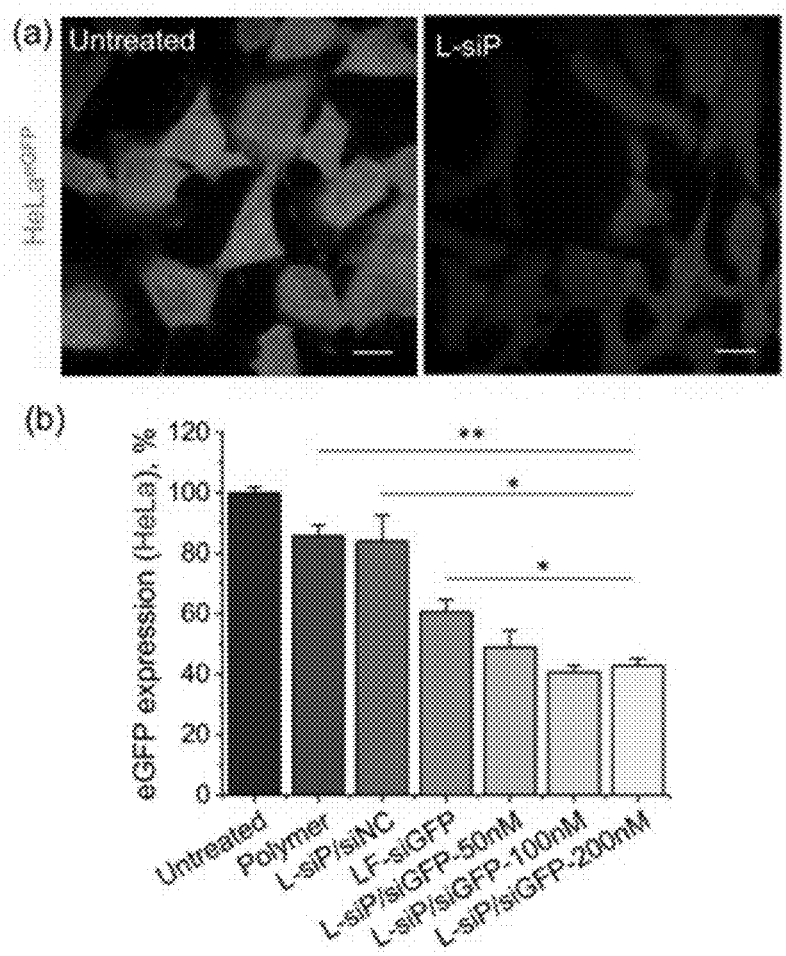
FIG. 6. eGFP silencing with L-siP15/1: Confocal microscopy images (a, b) for eGFP silencing and flow cytometry data (c) for quantification of eGFP fluorescence in HeLaeGFP cells; scale: 20 µm; Student's t-test: *p<0.001, p<0.01, *p<0.05, ns (non-significant)>0.05.

Gene Silencing Efficacy and Retrieval of Cytotoxicity Mediated Through PLK1 & MDR1 siRNAs Finally, the efficacy of the L-siP15/1 assembly in silencing specific gene activity was studied. To this end, HeLaeGFP and DU-145eGFP cells, stably expressing eGFP, were treated with L-siP15/1 nanoassembly containing 50, 100 and 200 nM GFP-siRNA. The reduction of green fluorescent intensity was evaluated through CLSM and flow cytometry (FIG. 6, S18). CLSM images, shown in FIG. 6a and S18a, reveals a clear decrease in green fluorescence intensity for both HeLaeGFP and DU-145eGFP cells upon treatment of L-siP15/1 nanoassembly. Further, the GFP expression (quantified through flow cytometry, FIG. 6b & S18b) was decreased to 43% at 200 nM siRNA concentration (L-siP/siGFP) in HeLaeGFP cells in comparison to ~84% for negative control siRNA (L-siP/siNC) treated cells. A similar trend was also observed in DU-145eGFP cells where L-siP/siGFP and L-siP/siNC treated cells showed 50% and 110% eGFP expression, respectively. Lipofectamine RNAiMAX-eGFP siRNA complex (LF-siGFP), evaluated as positive controls, exhibited reduction of eGFP expression up to 61% and 33% for HeLaeGFP and DU-145eGFP cells, respectively at similar siRNA concentrations.

Figure 7:
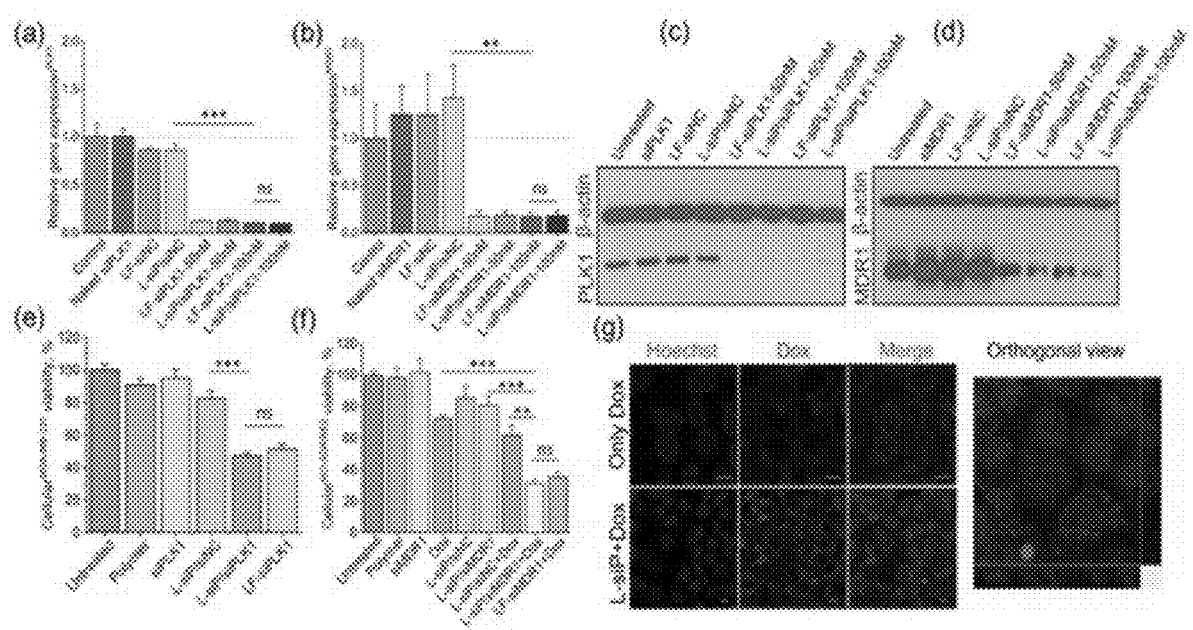
FIG. 7. Gene silencing study: qRT-PCR (a, b) and western blot (c, d) analysis for (a, c) PLK1 and (b, d) MDR1; Cellular viability mediated by knock-down of (e) PLK1 gene and (f) MDR1 gene (after treatment of doxorubicin for MDR1). Uptake comparison of doxorubicin via confocal microscopy (g) in untreated and L-siP/siMDR1 treated cells; orthogonal view is for L-siP+Dox sample; scale: 10 µm; Student's t-test: *p<0.001, p<0.01, *p<0.05, ns (non-significant)>0.05.
Figure 8:
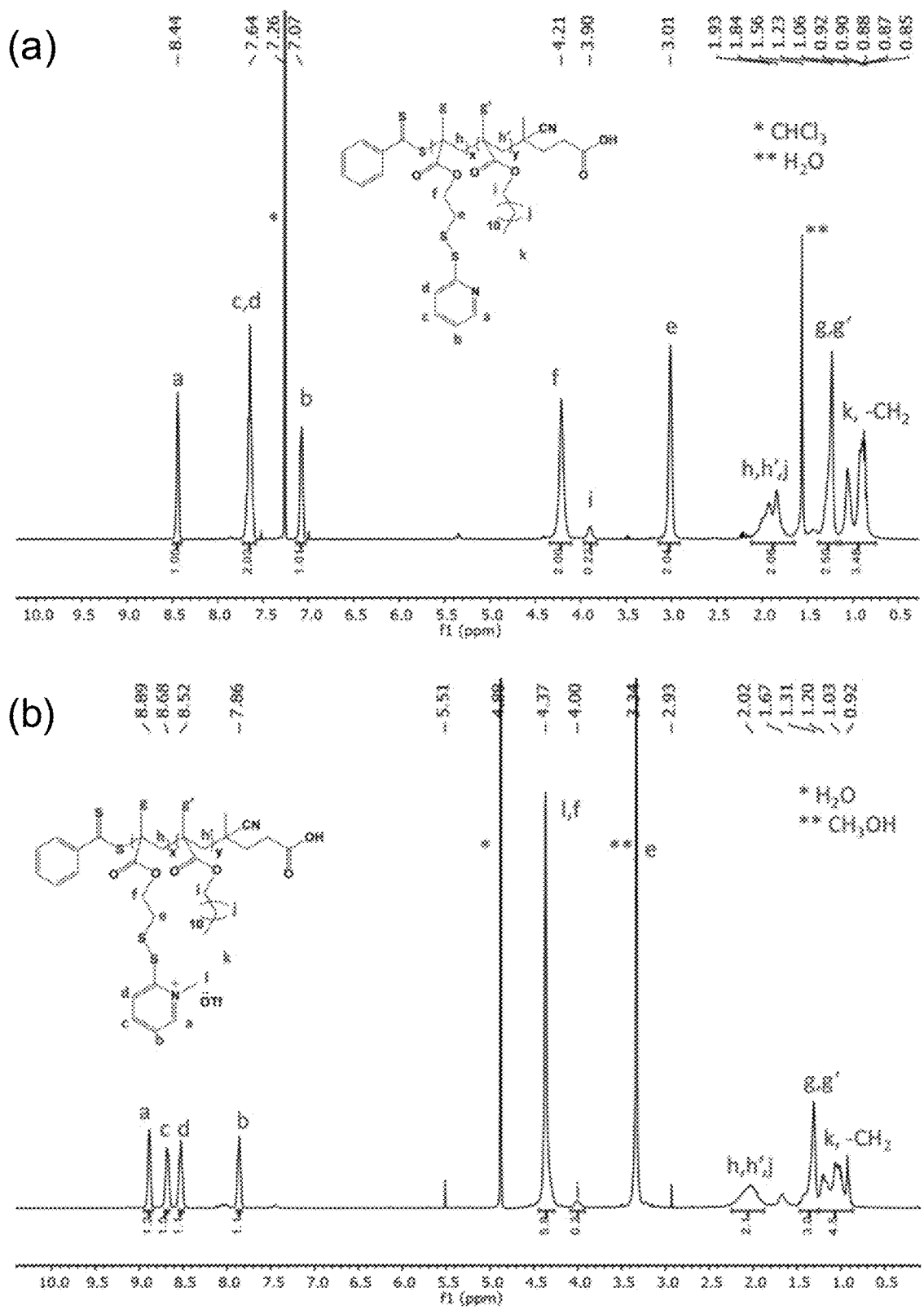
FIG. 8. $^{1}$H NMR spectra of (a) $P^{PDS/DD}$ and (b) $\oplus P^{PDS/DD}$ polymers.
Figure 9:
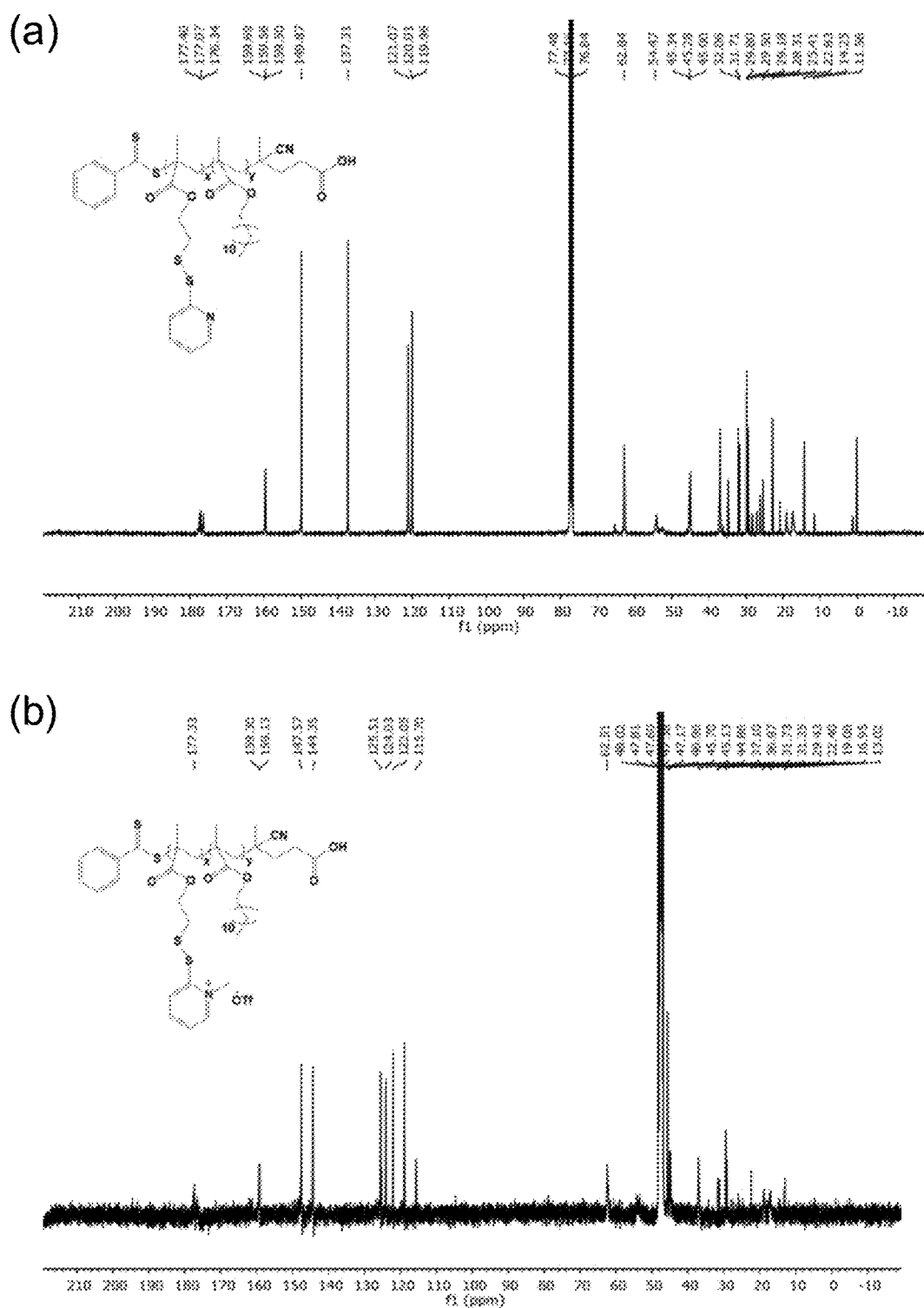
FIG. 9. $^{13}$C NMR spectra of (a) $P^{PDS/DD}$ and (b) $\oplus P^{PDS/DD}$ polymers.
Figure 10:
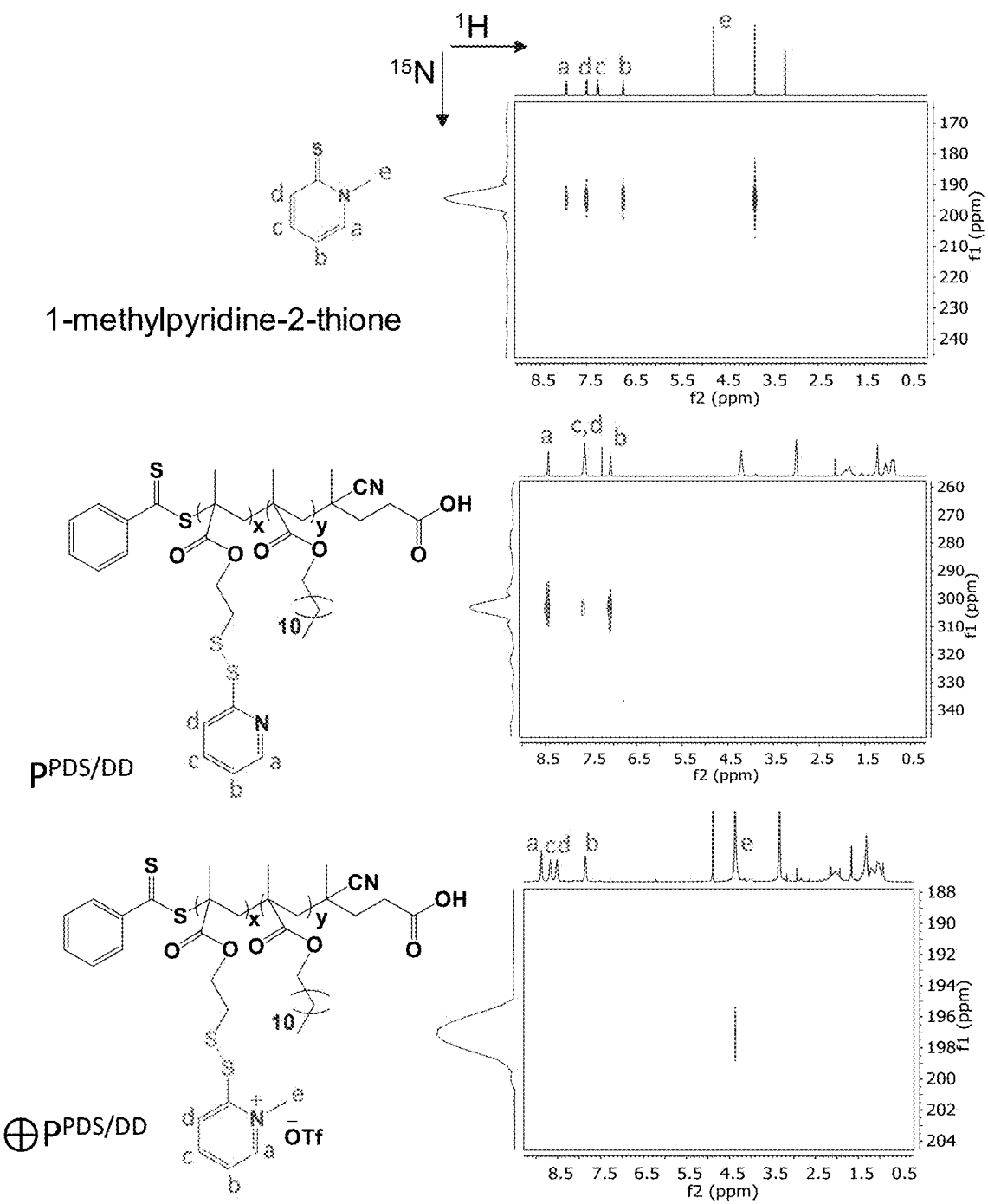
FIG. 10. $^{1}$H-$^{15}$N HMBC spectra of 1-methylpyridine-2-thione, $P^{PDS/DD}$ and $\oplus P^{PDS/DD}$ polymers. The absence of some correlation peaks with ring protons for the $\oplus P^{PDS/DD}$ polymer can be attributed to the short $T_2$ (spin-spin) relaxation which can be approximately calculated as, $T_2 \approx 1/(\pi\delta_{1/2})$, where δ is peak width at half height. For macromolecules like polymers, signals from protons with short $T_2$ often do not survive the 2D pulses that keep magnetization along xy plane. This also suggests slower molecular reorientation of cationic pyridine ring protons compared to the N-methyl protons. (Bloembergen, et al. 1948 Phys. Rev. 73 (7), 679-712.)
Figure 11:
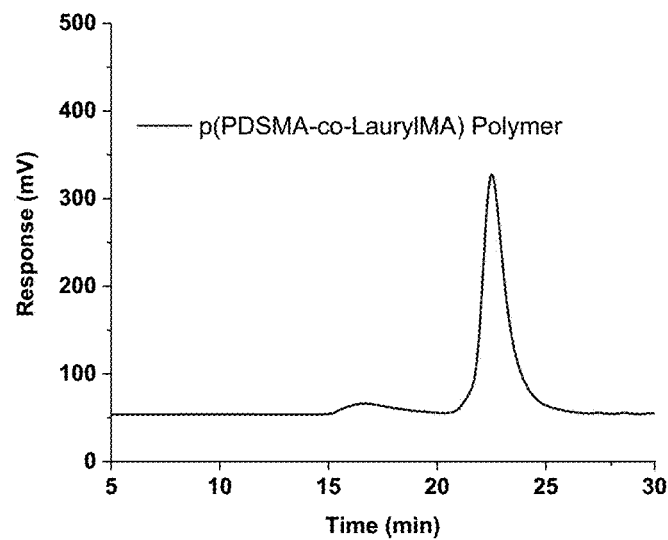
FIG. 11. Gel permeation chromatography of $P^{PDS/DD}$ polymer.
Figure 12:
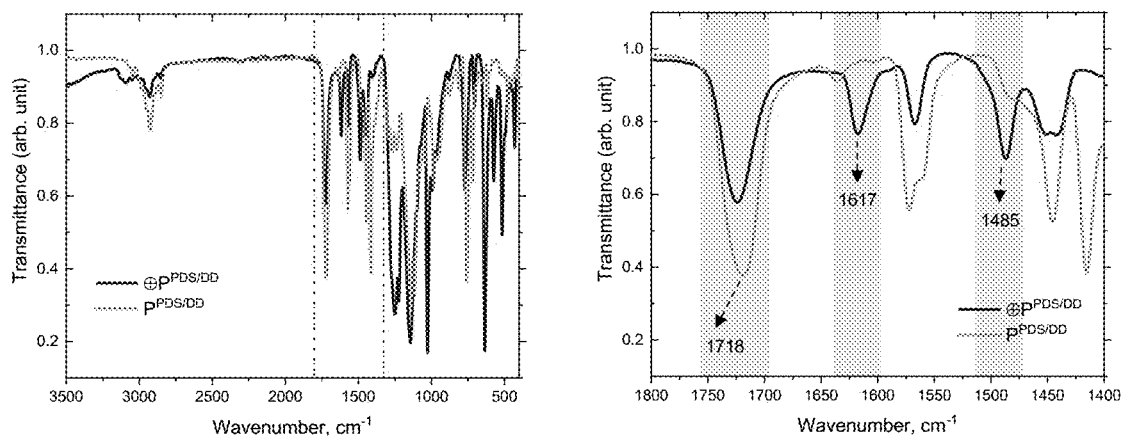
FIG. 12. FT-IR spectra of $P^{PDS/DD}$ and $\oplus P^{PDS/DD}$ polymers. A band at 1617 cm$^{-1}$ is observed for N-methylated pyridinium polymer ($\oplus P^{PDS/DD}$) characteristic of C=N vibration related to quaternary nitrogen atom in the ring. This band is absent in the $P^{PDS/DD}$ polymer. The pyridine ring low intensity band $\oplus P^{PDS/DD}$ polymer) at 1485 cm$^{-1}$ due to conjugated C=C and C=N bonds become stronger in the $\oplus P^{PDS/DD}$ polymer spectra. C=O stretching at 1718/1722 cm$^{-1}$ is used as calibration peak for both polymers. (Cook 1961 J. Chem. 39 (10), 2009; Katcka, et al. 1964 Bull. Acad. Pol. Sci., Ser. Sci., Chim., Geol. Geogr. 12 (9), 615.)

Encouraged by these results, tests were performed on the gene knock-down efficacy of the L-siP15/1 nanoassemblies towards two other gene types, PLK1 and MDR1, through evaluation of mRNA transcription levels by quantitative real-time polymerase chain reaction (qRT-PCR) and protein expressions by western blot analysis (FIG. 7). PLK1, a critical controller of mitosis, is found to be overexpressed in many cancer cells, leading to faster tumor progression. (Jiang, et al. 2015 Angew. Chem., Int. Ed. 54 (2), 506-510.) On the other hand, MIDR1 gene in multi-drug resistant cells upregulates the expression of drug transporter proteins, like P-glycoprotein (P-gp). (Xiong, et al. 2011 ACS Nano 5 (6), 5202-13.) Although various small molecule inhibitors for PLK1 and MDR1 are reported in literature, siRNA-based silencing is considered to be advantageous due to its specificity, much reduced toxicity and wide applicability in multiple cancer cells. L-siP assemblies were separately constructed based on PLK1- & MDR1-siRNA and evaluated the gene knock-down efficacy in MDA-MB-231 and NCI-ADR/RES cell lines, respectively. qRT-PCR studies showed efficient silencing of both PLK1 and MDR1 genes as evident by the reduced relative gene expression levels of ~12-18% in cells treated with L-siP nanoassemblies containing PLK1 and MDR1 siRNAs (FIGS. 7a and 7b, at 50 or 100 nM siRNA concentrations). Moreover, western blot analyses (FIGS. 7c, 7d and S19) revealed that PLK1 and P-gp protein expressions were reduced to ~25% and ~31% (~24% and 51% for lipofectamine), respectively compared to untreated cells.

To further demonstrate the consequence of L-siP nanoassembly mediated siRNA delivery and gene silencing, cellular viability studies were conducted on both PLK1 and MDR1 transfected MDA-MB-231 and NCI-ADR/RES cell lines, respectively. For PLK1 compromised cells (FIG. 7e), viability was reduced to ~47% for L-siP nanoassembly (~51% for lipofectamine positive control). Similarly, when treated with anti-cancer drug-doxorubicin (Dox), MDR1 depleted NCI-ADR/RES cells showed mere ~31% viability compared to ~73% and ~35% for free Dox and lipofectamine transfected positive control cells, respectively (FIG. 7f). (Zhang, et al. 2016 Sci. Rep. 6, 23859.) Moreover, CLSM images (FIG. 7g) confirm significantly higher red fluorescence intensity in cells from Dox indicating efficient penetration of the drug in L-siP nanoassembly (MDR1-siRNA) treated cells, whereas a rather subdued red fluorescence is observed for only free drug-treated cells.

Experimental

1. Materials

Dodecyl methacrylate, 2,2'-dithiodipyridine, 4-cyano-4-(phenylcarbonothioylthio)pentanoic acid, D, L-dithiothreitol (DTT), Glutathione were obtained from Sigma-Aldrich, USA and were used without further purification unless otherwise mentioned. 2,2'-azobis-(2-methylpropionitrile) (AIBN) was procured from Sigma-Aldrich, USA and purified by recrystallization before usage. Methyl trifluoromethanesulfonate was procured from Matrix Scientific, USA. Pyridyl disulfide ethyl methacrylate (PDSMA) was synthesized using previously reported procedure. (Ghosh, et al. 2006 Macromolecules 39 (17), 5595-5597.) 1,2-dioleoyl-sn-glycero-3-phosphoethanolamine (18:1 (Δ9-Cis) PE: DOPE) and 1,2-distearoyl-sn-glycero-3-phosphoethanolamine-N-[methoxy(polyethylene glycol)-2000](ammonium salt, DSPE-PEG2000) lipids were procured from Avanti Polar Lipids. Silencer™ Negative Control No. 1 siRNA (Catalog #: AM4611, proprietary sequence not provided), Silencer™ Cy™3-labeled Negative Control No. 1 siRNA (Catalog #: AM4621, proprietary sequence not provided), Silencer™ GFP (eGFP) siRNA (Catalog #: AM4626, proprietary sequence not provided) and MDR1/ABCB1-siRNA (sense: 5'-GCUUAACACCCGACUUACAtt-3', antisense: 5'-UGUAAGUCGGGUGUUAAGCtc-3') were procured from Thermo-Fisher Scientific. PLK1-siRNA was obtained from Qiagen, USA (sense: 5'-CGGGCAAGAUUGUGCC-UAATT-3', antisense: 5'-UUAGGCACAAUC-UUGCCCGCG-3'). Lipofectamine RNAiMAX, LysoTracker™ Blue DND-22, were obtained from Thermo-Fisher Scientific. Phosphorothioate siRNA (PTsi) was obtained from Dharmacon (sense: A*U*G*U*A*U*U*G*G*C*C*U*G*U*A*U*U*A*G, antisense: C*U*A*A*A*U*A*C*A*G*G*C*C*A*A*U*A*C*A*U; *denotes phosphorothioate modifications).

2. Synthesis of Polymers (a) Synthesis of p(PDSMA-Co-DodecylMA) Polymer ($P^{PDS/DD}$)

Reversible Addition-Fragmentation chain Transfer (RAFT) polymerization was utilized to synthesize p(PDSMA-co-DodecylMA) Polymer. In a typical procedure, PDSMA (0.903 g, 3.5 mmol), dodecyl methacrylate and chain transfer agent 4-cyano-4-(phenylcarbonothioylthio)pentanoic acid were taken in a 25 mL Schlenk flask and dissolved in 2 mL dry THF. To this mixture, 1.1 mg (0.007 mmol) AIBN, dissolved in 1 mL dry THF, was added. The solution was mixed for 5 min, the flask was subjected to three freeze-pump-thaw cycles and purged with argon. Finally, the sealed flask was transferred to a preheated oil-bath and the polymerization was carried out at 70° C. for 24 h. After that, the Schlenk flask was cooled down to quench the reaction and THE was evaporated. The reaction mixture was purified by precipitating in diethyl ether for three times and finally dried in vacuo for overnight at room temperature. Yield: 78%, GPC (THF) $M_n$: 14.5 kDa, Đ: 1.3; $^1$H NMR (400 MHz, CDCl$_3$): δ ppm 4.24-4.09, 3.87, 3.65-3.53, 3.37, 2.95-2.90, 1.93-1.84, 1.04-0.89; $^{13}$C NMR (100 MHz, CDCl$_3$): δ ppm 177.4, 177.07, 176.34, 159.69, 159.56, 159.5, 149.87, 137.31, 121.07, 120.01, 119.96, 62.84, 54.47, 45.34, 45.28, 45.00, 32.06, 31.71, 29.80, 29.50, 29.18, 25.41, 22.83, 14.25, 11.56.

(b) Synthesis of Cationic-PDS-Dodecyl Polymer (⊕$P^{PDS/DD}$)

In a 20 mL glass vial, 0.75 g of $P^{PDS/DD}$ polymer was weighed and dissolved in 5 mL DCM. The solution was cooled in ice for 10 min and after that methyl trifluoromethanesulfonate (0.73 g, 4.4 mmol) was added to it dropwise. The mixture was stirred at 4° C. overnight, the solvent was dried and precipitated in diethyl ether three times to purify. The polymer was dried overnight in vacuo at room temperature. Yield: 75%, calculated $M_n$: ~22 kDa; $^1$H NMR (400 MHz, CDCl$_3$): δ ppm 4.24-4.09, 3.87, 3.65-3.53, 3.37, 2.95-2.90, 1.93-1.84, 1.04-0.89; $^{13}$C NMR (100 MHz, CDCl$_3$): δ ppm 177.33, 159.3, 159.13, 147.57, 144.35, 125.51, 124.03, 122.05, 115.7, 62.51, 45.7, 45.13, 44.86, 37.1, 36.97, 31.73, 31.35, 29.43, 22.4, 19.08, 16.95, 13.02.

3. Characterization of Polymers (a) Gel Permeation Chromatography (GPC)

GPC of $P^{PDS/DD}$ polymer was performed in Agilent 1260 LC instrument with a refractive index detector using THE as the eluent and molecular weights were calculated against poly(methyl methacrylate, PMMA) standards.

(b) $^1$H, $^{13}$C, $^1$H-$^{15}$N & $^{31}$P NMR $^1$H, $^{13}$C and $^{31}$P NMR spectra of the samples were recorded on a Bruker NMR spectrometer (400.13 MHz for $^1$H, 100.62 MHz for $^{13}$C & 161.97 MHz for $^{31}$P). 2D NMR ($^1$H-$^{15}$N Heteronuclear Multiple Bond Correlation, HMBC) correlation spectra were acquired on Bruker NMR spectrometer (500.13 MHz for $^1$H, 50.68 MHz for $^{15}$N).

Molar ratio between the PDSMA and DodecylMA monomers for $P^{PDS/DD}$ polymer was calculated from the ratio of the integrations of —CH$_2$ protons adjacent to the methacrylate monomers (PDSMA, δ 4.21 and DocecylMA, δ 3.9 with x:y=9:1). (Gonzalez-Toro, et al. 2012 J. Am. Chem. Soc. 134 (16), 6964-6967; Dutta, et al. 2017 J. Am. Chem. Soc. 139 (16), 5676-5679.)

(c) FT-IR Spectra

FT-IR spectra of the polymers was recorded on a Bruker Alpha FT-IR (ATR) spectrometer from 3500 cm$^{-1}$-400 cm$^{-1}$ range.

4. Study of siRNA Encapsulation with Varying Dosage of ⊕$P^{PDS/DD}$ Polymer (at Different N/P Ratios)

(a) Preparation of L-siP Nanoassembly without Crosslinking

To study the effect of N/P ratio on complexation, two different sets of solutions were prepared containing siRNA and ⊕$P^{PDS/DD}$ in a mixed solvent system (acetone:water=70:30). In first set, a fixed amount of siRNA (2 μg) was dosed in acetone/water solvent mixtures (70:30) to get 50 μL identical solutions. In another set, different amounts ⊕$P^{PDS/DD}$ polymer solution (2 mg/mL in acetone:water=70:30) were diluted with same mixed solvent system to achieve another 50 μL solutions. Afterwards, the polymer solutions were added to the fixed amount siRNA solutions (containing 2 μg siRNA) to finally achieve N/P ratios of 5, 7.5, 10, 15, 20 and 25. All these mixed solutions were incubated for 2 h in an orbital shaker at 20° C. to facilitate complexation. Meanwhile, mix lipid solutions were prepared in 2 mL water containing 20% wt./wt. DOPE & 10 mol % DSPE-PEG (based on ⊕$P^{PDS/DD}$ polymer) and stirred for 30 min. Next, each of 100 μL nanoassembly solutions, after 2 h complexation period, was added to an aqueous pool of lipid mixture and stirred for 3 h at 20° C. In this step, the glass vials were kept open to facilitate the evaporation of organic solvents and maturation/hardening of the nanoassemblies. Finally, the solutions were filtered through Amicon Ultra Centrifugal Filters MWCO 10 kDa to remove remaining organic solvents, purify and concentrate the solutions. The final volume of L-siP nanoassembly solutions was adjusted to 100 μL with nuclease-free deionized water.

(b) Preparation of L-siP Nanoassembly with Crosslinking

Crosslinking of L-siP nanoassemblies were achieved by introducing DTT solutions after the complexation step. Different amounts of DTT (0.1, 0.25, 0.5, 1 and 2 equivalents with respect to PDS moiety in $\oplus P^{PDS/DD}$ polymer) dissolved in acetone/water (70:30) mix solvent were added to the siRNA-polymer mixtures after 2 h complexation step. Each solution was incubated in an orbital shaker at 20° C. for another 2 h. After that all solutions were subjected to lipid locating step.

5. Visualization of L-siP Nanoassembly with N-STORM Confocal Microscope

For N-STORM imaging, cy3-labelled siRNA loaded L-siP nanoassemblies were prepared and the outer lipid layer of the nanoassembly was incorporated with carboxyfluorescein labelled PEG-lipid (18:0 PEG2000 PE CF). The particles were first deposited on a L-lysine coated 35 mm glass bottomed petri-dish and incubated at room temperature for 15 min. Next, excess solution was withdrawn and gently washed with nuclease free water to remove loosely bound particles. Finally, imaging buffers (5% m/v glucose, 0.1 M MEA, 1 mg/mL glucose oxidase and catalase) were added to the wet petri-dish and transferred to NIKON confocal/N-STORM set-up for imaging (100×TIRF objective, excitation at 488 & 561 nm).

6. Measurement of DLS and Zeta-Potentials for L-siP Nanoassemblies

Dynamic light scattering (DLS) and zeta potential measurements were performed using a Malvern Nanozetasizer-ZS. Prepared L-siP nanoassembly and control samples were diluted with Milli-Q water (50 μL sample added to 850 μL water) before subjected to particle size and zeta potential measurements.

7. Agarose-Gel Retardation Assay for Proof of Complexation & siRNA Release (a) Encapsulation Study 20 μL samples (with different N/P ratios and varying crosslinking) were mixed with 4 μL of gel loading buffer and loaded into 2% agarose gel made in TAE buffer containing EtBr. Samples were run in horizontal electrophoresis system at 110 V for 1 h and subjected to imaging analysis with NuGenius gel imager system (Syngene).

(b) Release Study

20 μL sample was mixed with 1 μL Triton-x (0.1 g/mL) and sonicated for 5 min. Next, 250 mM glutathione solution was added to it and the pH was adjusted to ~7-8 with 1 N NaOH solution (final glutathione concentration was 10 mM). The mixture was incubated for 6 h at 37° C. and subjected to agarose gel electrophoresis and visualization method as described above.

8. Cryo-TEM Study of L-siP Nanoassemblies-N/P 15-Crosslinked (1 Equiv DTT) & Uncrosslinked Cryo Transmission Electron Microscopy was performed using FEI (Fisher Scientific) Tecnai T12 instrument operated at 120 kV using a Gatan 636 cryo-transfer holder. Imaging was done under low dose conditions. Samples were prepared using a FEI (Fisher Scientific) Vitrobot MKII using liquid ethane. Lacey Carbon on 200 mesh Copper Grids were glow discharged for 30 s prior usage.

9. Quantification of siRNA Encapsulation & Release for L-siP Nanoassembly Through Quant-iT™ RiboGreen Assay To generate a standard curve of free siRNA, different concentrations of negative control siRNA solutions were prepared in nuclease-free water as per the manufacturer's protocol. (Jones, et al. 1998 *Anal. Biochem.* 265 (2), 368-374.) L-siP nanoassemblies encapsulated with negative control siRNA with differential crosslinking density were diluted with TE buffer and mixed with RiboGreen reagent in a black 96 well plate. Another set of L-siP nanoassemblies were subjected to glutathione mediated release condition (section 7b) at first; then mixed with buffer and RiboGreen reagent. Samples were incubated at room temperature for 5 min and then subjected to fluorescence measurements in SpectraMax® M5 fluorescence microplate reader (excitation: 480 nm, emission: 520 nm).

10. Stability of L-siP Nanoassembly in Presence of RNase a and Serum

To test the L-siP nanoassemblies stability in presence of RNase A, 15 μL of L-siP nanoassembly solution (N/P 15, 1 equiv DTT crosslinked) was mixed with 1 uL RNase A solution (50 μg/mL) or serum (10% v/v) and incubated at 37° C. for different time intervals. After that, 2 μL of EDTA (0.5 M) and 2 μL SDS (100 mM) were added to it and heated at 60° C. for 5 min. Afterwards, samples were subjected to glutathione (10 mM) based release conditions and finally loaded into 2% agarose gel (EtBr stained) to check the band intensity. For control, equal amount of naked siRNA was subjected to the identical conditions.

11. MD-Simulations: Modelling for Encapsulation & Release

CG models—The CG model for the cationic PDS-Dodecyl polymer ($\oplus P^{PDS/DD}$) has been built based on the popular MARTINI force field. (Marrink, et al. 2007 *J. Phys. Chem. B* 111(27), 7812-24.) The CG structure has been mapped from an all atom (AA) structure of the polymer, while the appropriate CG MARTINI beads have been selected to preserve the different hydrophobicity of the mapped chemical groups (see FIG. 14 for details). Experiments have been conducted using double strand dsRNA fragments, which are rigid charged molecules. For convenience, the CG simulations have been conducted using rigid 20-bp dsDNA segments of the same length instead of RNA, given the availability of a reliable MARTINI model for DNA (using dsDNA instead of dsRNA make little difference in the models, as the aggregation is controlled by electrostatic interactions and that can be both thought of as rigid charged cylindrical molecules). DTT has been mapped consistently on an AA model. The DTT CG model is composed of four CG beads—two central SP2 beads plus two terminal SC5 beads. The interaction between the DTT terminal SC5 beads and the first SC5 bead of the PDSMA chains has been then artificially strongly enhanced, to mimic the effect of DTT crosslinking ((i) strong selective spontaneous coordination and (ii) formation of stable bonds—see also FIG. 15).

Simulation parameters—All simulations have been performed with the GROMACS molecular dynamics suite, patched with the PLUMED plugin. (Berendsen, et al. 1995 *Comput. Phys. Commun.* 91 (1), 43-56; Tribello, et al. 2014 *Comput. Phys. Commun.* 185 (2), 604-613.) In production runs, the MD integrator was used with a time step of 20 fs, the v-rescale thermostat with a time constant of 2 ps and the Parrinello-Rahman barostat with a time constant of 8 ps. (Bussi, et al. 2007 *J. Chem. Phys.* 126 (1), 014101; Parrinello, et al. 1981 *J. Appl. Phys.* (Melville, NY, U.S.) 52 (12), 7182-7190.)

Aggregation in N/P 7.5 and N/P 15 systems—The two systems were built by inserting 6 (or 12) dsDNA chains in a simulation box containing the same amount (58) of cationic polymer chains, a 70:30 acetone:water mixture and monovalent counterions to ensure charge neutrality of the system. In both systems, spontaneous aggregation was observed between the dsDNA fragments and the cationic polymer chains, led by the electrostatic interaction between their oppositely charged groups. The final aggregates in 70:30 acetone:water appeared as quite loose and not very dense (see FIG. 16), consistent with experimental observations of the systems before the insertion of DTT.

DTT crosslinking—The effect of crosslinking has been mimicked in two steps: (i) the insertion of DTT molecules that selectively bind to the S—S groups of the polymers and (ii) the cleavage of positively charged groups of the polymers. For (i), an artificially strong interaction was first imposed between the terminal DTT CG beads and the first SC5 beads in the side charged groups of the polymer (FIG. 15)—this allowed us to model the spontaneous coordination of DTT to those side groups that are really accessible by DTT molecules. Then (ii), the side charged groups coordinated to DTT have been detached from the rest of the polymer (deletion of the explicit bonds), and the SQ0 bead has been turned neutral, consistent with the experimental process.

Creation of the L-siP nanoparticle for the N/P 15 system—To create a model of the L-siP nanoparticle, starting from the self-assembled polymer-dsDNA system at N/P 15 and a 100% crosslinking was introduced as described above. The 70:30 acetone:water mixture was replaced with a (more polar) 20:1 water:acetone solvent mixture, coherent with the experiments, and introduced in the system enough DOPE lipids to cover the assembled aggregate surface. In order to obtain a single aggregate at the center of the simulation box, a recently optimized simulation technique (involving the use of PLUMED plugin) was used that drives the spontaneous assembly of self-assembling molecules toward a single aggregation center (instead of forming multiple nuclei, which slow down the aggregation process). (Bochicchio, et al. 2017 *J. Phys. Chem.* Lett. 8 (16), 3813-3819.) The system has been then equilibrated for 4 μs of CG-MD simulation. The radial distribution functions of FIG. 2*f* have been calculated with the gmx rdf tool of the GROMACS suite and normalized to have the same integral.

Release simulations—To model the release of dsDNA fragments at different crosslinking conditions, L-siP nanoparticle at N/P 15 ratio and 100% of crosslinking (1 equiv DTT) were equilibrated. The DOPE lipid molecules were removed and 3 different simulations were performed: one keeping all coordinated DTT in the system (100% crosslinking), one removing 90% of the DTT molecules (thus, effectively simulating a residual 10% crosslinking condition) and a last one removing all the DTT (0% residual crosslinking). The dsDNA release has been quantified by monitoring the number of contacts between the polymer and the guest oligos in time during the CG-MD run calculated with gmx mindist and normalized dividing by the initial value (corresponding to the equilibrated L-siP nanoparticle).

12. Cell culture

HeLa (cervical cancer), DU 145 (prostate cancer), MDA-MB-231 (mammary gland/breast cancer), NCI/ADR-RES (derived from the ovarian cell line OVCAR-8/Adriamycin (Doxorubicin or Dox) resistant, procured from NCI, Frederick), HeLa$^{eGFP}$ and DU 145$^{eGFP}$ (eGFP transfected) cell lines were cultured in 100 mm cell culture petri-dish containing Dulbecco's Modified Eagle Medium/Nutrient Mixture F-12 (DMEM/F12) in a humidified incubator with 5% $CO_2$ at 37° C. Culture media was supplemented with 10% fetal bovine serum (FBS), 1% L-glutamine and 1% antibiotic-antimycotic (100 units/mL of penicillin, 100 μg/mL of streptomycin, and 0.25 μg/mL of Amphotericin B).

13. Cellular Internalization Studies (a) Confocal Microscopy

HeLa, DU 145 and MDA-MB-231 cell lines were seeded at $1\times10^5$ cells/mL density (1 mL) in 35 mm glass-bottomed petri-dishes and cultured for 3 days at 37° C. and 5% $CO_2$ incubator for proper adhesion. Afterwards cells were washed three times with PBS buffer and incubated with L-siP nanoassemblies containing 100 nM cy3-siRNA in 1 mL serum-free media at 37° C. for 4 h. Next, the media was removed, washed three times with PBS and incubated with NucBlue™ Live ReadyProbes™ reagent in FBS containing media for 1 h to stain cell nucleus. Live cell imaging was performed using Nikon Spectral A1+ confocal microscope. All images were analyzed with Nikon NIS-Elements software.

(b) Flow Cytometry for Uptake Quantification

HeLa, DU 145 and MDA-MB-231 cell lines were seeded at $1\times10^5$ cells/mL density (1 mL) in 12 well plate and cultured for 1 day at 37° C. and 5% $CO_2$ incubator. Next, cells were washed three times with PBS buffer and incubated with L-siP nanoassemblies containing 100 nM cy3-siRNA in 1 mL serum-free media at 37° C. for 4 h. Next, cells were washed with cold PBS and trypsinized (0.25% trypsin-EDTA solution) for 10 min to remove non-internalized samples from cell surface and de-touch from well plate. Cells were pelleted by centrifugation, washed two times with cold PBS and finally re-suspended with 500 μL cold PBS for flow cytometry analysis in BD LSRFortessa™ instrument. Data analyses was performed with FlowJo software to obtain fluorescence intensities of cell samples.

(c) Mechanism of Cellular Uptake

HeLa, DU 145 and MDA-MB-231 cell lines were seeded at $1.2\times10^5$ cells/mL density (1 mL) in 12 well plate and cultured for 1 day at 37° C. and 5% $CO_2$ incubator. Next, cells were washed with PBS and pre-incubated with EIPA (100 μM, macro-pinocytosis pathway), Nystatin (30 μM, caveolin pathway) and Hyper-osmolar sucrose (45 mM, clathrine pathway) in serum-free media for 1 h at 37° C. After pre-incubation step, cells were co-incubated for another 1 h with L-siP nanoassemblies loaded with cy3-siRNA (50 nM, 1 mL serum-free media) and different inhibitors with final concentrations mentioned above. Untreated and L-siP-cy3-siRNA treated cells without any inhibitor were used as negative and positive controls, respectively. Next, cells were harvested as described above (section 13b) for flow cytometry analysis.

14. Endosomal Escape

MDA-MB-231 cells were seeded at $1.5\times10^5$ cells/mL density (1 mL) in 35 mm glass-bottomed petri-dishes and cultured for 1 day at 37° C. and 5% $CO_2$ incubator.

(a) Colocalization of Lysotracker Blue-Cy3 siRNA

To study the endosomal escape, cells were washed with PBS three times and incubated with 100 nM cy3-siRNA L-siP nanoassemblies for 4 h in serum-free media. Next, one set of samples was subjected to confocal imaging after endosome staining and the other set was incubated for 24 h in complete media before subjecting to endosome staining and confocal microscopy. Lysotracker blue was used to stain endosomes as per manufacturer's protocol. Live cell imaging was performed using Nikon Spectral A1+ confocal microscope. To improve visibility, Lysotracker Blue stain in the images was pseud-colored with green and colocalization with red cy3-siRNA was studied. All images were analyzed with Nikon NIS-Elements 4.0 software.

(b) Calcein Assay

Cells were transfected with negative control siRNA loaded L-siP nanoassembly (100 nM siRNA) and 100 μM calcein for 8 h in serum-free media. Next, those were washed three times with PBS and incubated with complete media for another 2 h. A control set of cells was generated with only calcein treatment (without L-siP). Before subjecting to CLSM study, cell nucleus was stained with NucBlue™ Live ReadyProbes™ reagent. Cells were imaged with Nikon Spinning Disk Confocal Microscope (excitation 488 nm laser) and data was analysed with Nikon NIS-Elements software.

15. Toxicity Studies of L-siP Nanoassemblies in HeLa/DU-145/MDA-MB-231 Cell Lines (a) AlamarBlue Assay for Cellular Viability HeLa, DU 145 and MDA-MB-231 cells were seeded ($7.5 \times 10^3$ cells in 0.1 mL per well) into 96-well tissue culture plates and incubated at 37° C. After 24 h, cell culture media was replaced with serum-free media containing L-siP nanoassemblies bearing different concentrations of negative control siRNA (25, 50, 100, 200 and 500 nM). Identical control crosslinked nanoassemblies devoid of any siRNA, L-siP (empty), were also tested for toxicity. Lipofectamine® RNAiMAX was complexed at different dosages (2, 5 and 10 μL/mL) with negative control siRNA (100 nM) and compared with other samples. After 24 h incubation (4 h for Lipofectamine samples), media was replaced with complete fresh one and incubated for another 2 days (72 h in total). After that cells were washed with PBS for three times and each well was treated with 100 μL 10% alamarBlue in complete media. Finally, cells were incubated for 1 h at 37° C. and solutions were transferred to black 96-well flat-bottomed plate for fluorescence measurement with SpectraMax® M5 microplate reader (excitation: 560 nm, emission: 590 nm).

(b) LDH Cytotoxicity Assay for Membrane Damage Studies

For LDH assay, all cells were incubated with L-siP nanoassembliess for 24 h and then subjected to Pierce LDH cytotoxicity assay. (Korzeniewski, et al. 1983 *J. Immunol. Methods* 64 (3), 313-20.) 50 μL of media was collected from 96 well cell culture plate and transferred to another 96 well plate. To that solution 50 μL LDH reaction mixture was added and incubated at room temperature for 30 min. Next, 50 μL stop solution was added to each well and subjected to absorbance measurements with SpectraMax® M5 microplate reader at 490 nm and 680 nm (cytotoxicity was calculated based on absorbance, $A = A_{490} - A_{680}$).

16. Gene Silencing Studies
(a) Knockdown of GFP in GFP-Transfected HeLa & DU-145 Cell Lines Through Flow Cytometry & Confocal Microscopy To study the gene silencing, GFP-transfected HeLa and DU-145 cells were plated in 12 well plate ($5 \times 10^4$ cells in each well) and incubated for 24 h at 37° C. After that cells were transfected with GFP-siRNA loaded L-siP nanoassemblies (50, 100 & 200 nM siRNA concentrations) and incubated for 24 h. Next, media was replaced with fresh one and incubated for another 24 h at 37° C. Finally, cells were trypsinized, pelleted by centrifugation and washed two times with PBS followed by suspension in 500 μL PBS. Flow cytometry was performed with this cell suspension in a BD LSRFortessa™ instrument (excitation wavelength: 488 nm, FITC channel) to check the reduction in GFP fluorescence intensity. FlowJo version 10 software was used to analyze data and obtain fluorescence intensities of the samples.

For confocal microscopy analyses for GFP-silencing, $1 \times 10^5$ cells were plated in 35 mm glass-bottomed petri-dishes and incubated for 3 days at 37° C. and 5% $CO_2$ incubator for proper adhesion. Afterwards cells were transfected with L-siP-GFP-siRNA nanoassemblies, incubated for 24 h, washed and subjected to further 24 h incubation before subjecting to washed three times with PBS buffer and incubated with L-siP nanoassemblies containing 100 nM cy3-siRNA in 1 mL serum-free media at 37° C. for 24 h. Next, the media was removed, washed three times with PBS and incubated with NucBlue™ Live ReadyProbes™ reagent in FBS containing media for 1 h to stain cell nucleus. Live cell imaging was performed using Nikon Spinning Disk confocal microscope. All images were analyzed with Nikon NIS-Elements software.

(b) Knockdown of PLK1 in MDA-MB-231 and MDR1 in NCI-ADR/RES Cell Lines Through qPCR & Western Blot Studies $1.5 \times 10^5$ cells were plated in 6 well tissue culture plate, incubated for 24 h at 37° C.-5% $CO_2$ atmosphere and then transfected with L-siP nanoassemblies containing PLK1 and MDR1 siRNA (at 50 & 100 nM siRNA concentration) for MDA-MB-231 & NCI-ADR/RES cells, respectively. Control samples containing L-siP nanoassemblies without siRNA, untreated cells and only siRNA treated cells were subjected to similar conditions. After transfection (24 h), media was changed and incubated at 37° C.-5% $CO_2$ atmosphere for another 24 h.

qPCR Studies

Finally, cells were washed and total RNA was isolated by RNA extraction kit (High Pure RNA Isolation Kit, Roche) according to manufacturer's protocol. Isolated RNAs were checked for purity and concentrations by measuring absorbances at 260/280 nm.

Next, cDNA synthesis was performed with iScript cDNA synthesis kit (Bio-Rad Laboratories) from the isolated RNA. After that, RT-PCR was performed using the synthesized cDNA, PerfeCTa MultiPlex qPCR SuperMix (Low ROX) and Taqman probes for PLK1, MDR1 and control β-actin genes in Mx3005P qPCR System (Stratagene/Agilent). Target gene expression levels were normalized and reported as fold increase compared to β-actin using the ΔΔCT method.

Western Blot Analyses

To isolate total proteins, cells were washed with cold PBS buffer once and scraped to de-touch from the plate and transferred with cold PBS to an eppendorf tube. Afterwards, cells were pelletized by centrifugation, washed with cold PBS twice to remove proteins from media.

Next, RIPA lysis buffer containing protease/phosphatase inhibitor mix was added to the cell pellet keeping it in ice and incubated for 15 min, followed by 3×30 s sonication to ensure complete lysis of cells. Finally, lysed cells were centrifuged at 14000 rpm-4° C. to collect soluble protein extracts and quantified with 660 nm protein assay.

Western blot analyses were performed to identify PLK1 and MDR1/P-gp protein levels in cells. Rabbit monoclonal antibodies (PLK1, MDR1/ABCB1 & β-Actin mAbs, Cell Signaling) were used to detect target proteins and loading control. HRP-linked anti-rabbit IgG was used as secondary antibody and proteins bands were detected by enhanced chemiluminescence (ECL) reagent (Luminol, coumaric acid and $H_2O_2$).

17. Cellular Viability Post-PLK1 and MDR1 Knockdown

MDA-MB-231 and NCI-ADR-RES cells were seeded at a density of $5 \times 10^3$ cells/well/100 μL in 96-well tissue culture plate. After 24 h incubation, media well removed and treated with L-siP nanoassemblies loaded with PLK1 siRNA (for MDA-MB-231 cells) and MDR1 siRNA (for NCI/ADR-RES) at final siRNA concentration of 100 nM in serum-free media. Control sets of samples were also subjected to identical conditions. After 24 h incubation, media was replaced with fresh complete one and incubated for another 48 h.

For PLK1 siRNA treated samples, cells were subjected to alamarBlue assay.

For MDR1-siRNA treated samples, media was removed, treated with 10 μM doxorubicin in complete media and incubated for another 48 h. After that cells were subjected to alamarBlue assay.

18. Uptake of Doxorubicin in NCI/ADR-RES Cells after MDR1 Knockdown

NCI/ADR-RES cells were seeded at $1 \times 10^5$ cells/mL density (1 mL) in 35 mm glass-bottomed petri-dishes and cultured for 3 days at 37° C. and 5% $CO_2$ incubator for proper adhesion. (Garraway, et al. 2005 Nature 436 (7047), 117-122; Alvarez, et al. 1995 J. Clin. Invest. 95 (5), 2205-14.) Afterwards, media was removed, treated with L-siP nanoassemblies loaded with MDR1-siRNA (final siRNA concentration: 100 nM) in serum-free media and incubated for 24 h. Next, media was replaced with fresh complete one and incubated for another 48 h. After that, cells were treated with 10 μM doxorubicin and incubated for 4 h. Finally, media was removed, cells were washed with PBS and nucleus was stained with NucBlue™ Live ReadyProbes™ reagent before subjecting to confocal microscopy by Nikon Spectral A1+ confocal microscope. All images were analyzed with Nikon NIS-Elements software.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compounds or compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Applicant's disclosure is described herein in preferred embodiments with reference to the FIG.s, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A molecular assembly, comprising:
 a crosslinked polymer-nucleic acid complex comprising a nucleic acid encapsulated in a crosslinked polymer network; and
 a coating on the crosslinked polymer-nucleic acid complex, wherein the coating comprises a zwitterionic lipid and a PEGylated lipid.

2. The molecular assembly of claim 1, wherein the crosslinked polymer-nucleic acid complex comprises:
 a crosslinked block or random copolymer comprising structural units of:

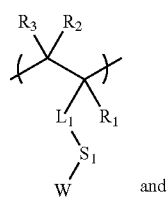

(I)

and

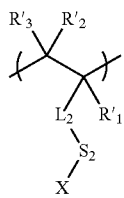

(IV)

wherein
- each of $R_1$ and $R'_1$ is independently a hydrogen, $C_1$-$C_{12}$ alkyl group, or halogen;
- each of $R_2$, $R'_2$, $R_3$, and $R'_3$ is independently a hydrogen, $C_1$-$C_{16}$ alkyl, $C_1$-$C_{16}$ alkyloxy, or halogen;
- each of $L_1$ and $L_2$ is independently a linking group;
- each of $S_1$ and $S_2$ is independently a single bond or a spacer group;
- W is a hydrophobic group; and
- X is a group comprising a crosslinking moiety; and
a nucleic acid molecule entrapped in the crosslinked block or random copolymer.

3. The molecular assembly of claim 2, wherein the block or random copolymer further comprises the structural unit of:

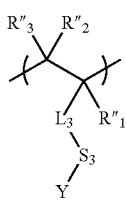

(III)

wherein
- $R''_1$ is a hydrogen, $C_1$-$C_{12}$ alkyl group, or halogen;
- each of $R''_2$ and $R''_3$ is independently a hydrogen, $C_1$-$C_{16}$ alkyl, $C_1$-$C_{16}$ alkyloxy, or halogen;
- $L_3$ is a linking group;
- $S_3$ is a single bond or a spacer group; and
- Y is a non-crosslinking group.

4. The molecular assembly of claim 2, wherein X comprises a crosslinked group.

5. The molecular assembly of claim 2, wherein X comprises a group capable of forming a crosslinking bond.

6. The molecular assembly of claim 2, wherein the nucleic acid molecule is selected from single-standed or double-stranded RNA or DNA, and derivatives or anologs thereof.

7. The molecular assembly of claim 2, wherein the nucleic acid molecule is selected from dsRNA, siRNA, mRNA, ncRNA, microRNA, catalytic RNA, gRNA, DNAs, oligonucleotides, aptamers, genes, plasmids, and derivatives or anologs thereof.

8. The molecular assembly of claim 7, wherein the nucleic acid molecule is an siRNA.

9. The molecular assembly of claim 2, wherein the copolymer is a random copolymer.

10. The molecular assembly of claim 2, wherein the copolymer is a block copolymer.

11. The molecular assembly of claim 2, wherein W comprises a $C_1$-$C_{30}$ linear or branched alkyl group.

12. The molecular assembly of claim 2, wherein each of $L_1$, $L_2$ and $L_3$ is independently a

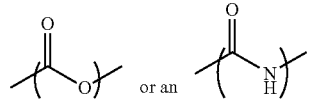

group.

13. The molecular assembly of claim 2, wherein X comprises a disulfide group.

14. The molecular assembly of claim 2, wherein the block or random copolymer further comprises the structural unit of:

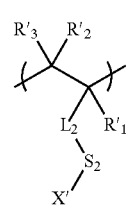

(II)

wherein X' comprises a group selected from:

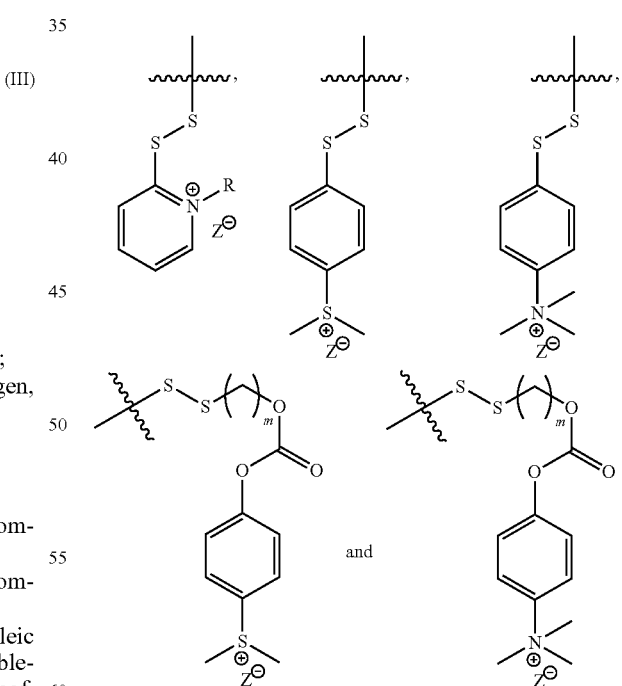

and wherein R is a $C_1$-$C_{15}$ alkyl group, and Z is a counter ion.

15. The molecular assembly of claim 2, being crosslinked both inter-molecularly and intra-molecularly.

16. The molecular assembly of claim 2, wherein the zwitterionic lipid comprises a zwitterionic group selected from the group consisting of:

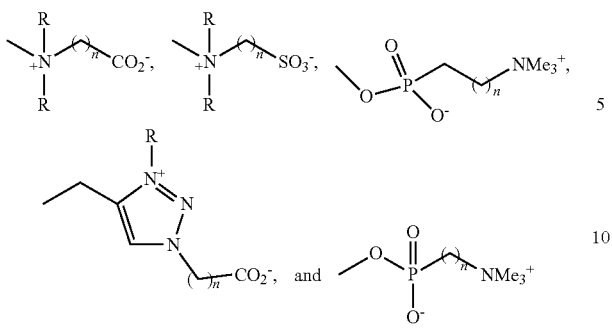
wherein each R is hydrogen or a $C_1$-$C_{15}$ alkyl group; n is independently an integer from about 1 to about 12.
17. The molecular assembly of claim 16, wherein each n is independently an integer from about 2 to about 6.
* * * * *